(12) United States Patent
Banerjee et al.

(10) Patent No.: US 10,575,771 B2
(45) Date of Patent: Mar. 3, 2020

(54) MULTI-PARAMETRIC MAGNETIC RESONANCE DIAGNOSIS AND STAGING OF LIVER DISEASE

(71) Applicant: Isis Innovation Limited, Oxford (GB)

(72) Inventors: Rajarshi Banerjee, Oxford (GB); Stefan Piechnik, Oxford (GB); Matthew Robson, Oxford (GB); Belen Rial, Oxford (GB); Elizabeth Tunnicliffe, Oxford (GB); Stefan Neubauer, Oxford (GB)

(73) Assignee: Oxford University Innovation Limited, Oxford (GB)

( * ) Notice: Subject to any disclaimer, the term of this patent is extended or adjusted under 35 U.S.C. 154(b) by 1651 days.

(21) Appl. No.: 14/364,750

(22) PCT Filed: Dec. 13, 2012

(86) PCT No.: PCT/GB2012/053116
§ 371 (c)(1),
(2) Date: Jun. 12, 2014

(87) PCT Pub. No.: WO2013/088149
PCT Pub. Date: Jun. 20, 2013

(65) Prior Publication Data
US 2014/0330106 A1 Nov. 6, 2014

Related U.S. Application Data

(60) Provisional application No. 61/630,508, filed on Dec. 13, 2011.

(30) Foreign Application Priority Data

Dec. 13, 2011 (GB) .................................. 1121404.6

(51) Int. Cl.
*A61B 5/00* (2006.01)
*A61B 5/055* (2006.01)
(Continued)

(52) U.S. Cl.
CPC ............ *A61B 5/4244* (2013.01); *A61B 5/004* (2013.01); *A61B 5/055* (2013.01); *A61B 5/4881* (2013.01);
(Continued)

(58) Field of Classification Search
None
See application file for complete search history.

(56) References Cited

U.S. PATENT DOCUMENTS 5,218,532 A 6/1993 Mori
5,322,682 A 6/1994 Bartzokis
(Continued)

FOREIGN PATENT DOCUMENTS

DE 102009011382 9/2010
GB 2498254 9/2010
(Continued)

OTHER PUBLICATIONS

Sirlin et al., Magnetic Resonance Imaging Quantification of Liver Iron, Magn Reson Imaging Clin N Am. Aug. 2010, 18(3).*
(Continued)

*Primary Examiner* — Bo Joseph Peng
(74) *Attorney, Agent, or Firm* — Thomas|Horstemeyer, LLP

(57) ABSTRACT

Described herein are systems and methods for performing multi-parametric diagnosis for liver disease. Systems and methods as described herein can include positioning a subject-in association with a medical imaging device and using the medical imaging device to measure the subject's liver for extracellular fluid and iron content. Systems and
(Continued)

methods as described herein can further include determining whether iron overload may be indicated or present from the measurement for iron content, and if indicated, correcting the measurement for extra cellular fluid. Systems and methods as described herein can further include measuring the liver for hepatic lipid content (HLC). Systems and methods as described herein can determine the presence or absence of liver disease from measurements obtained from a subject. In certain embodiments, the medical imaging device is a magnetic resonance (MR) scanner. In certain embodiments, the liver is measured for iron overload.

12 Claims, 23 Drawing Sheets

(51) Int. Cl.
G01R 33/48 (2006.01)
G01R 33/50 (2006.01)
G01R 33/46 (2006.01)
G01R 33/54 (2006.01)

(52) U.S. Cl.
CPC ........ *A61B 5/7282* (2013.01); *G01R 33/4828* (2013.01); *G01R 33/50* (2013.01); *G01R 33/46* (2013.01); *G01R 33/54* (2013.01)

(56) References Cited

U.S. PATENT DOCUMENTS

| | | | |
|---|---|---|---|
| 5,908,386 | A | 6/1999 | Ugurbil et al. |
| 5,993,398 | A | 11/1999 | Alperin |
| 6,245,027 | B1 | 6/2001 | Alperin |
| 6,605,943 | B1 | 8/2003 | Clark et al. |
| 2004/0102692 | A1 | 5/2004 | Schenck |
| 2004/0155653 | A1 | 8/2004 | Larson et al. |
| 2005/0197586 | A1 | 9/2005 | Pearlman |
| 2007/0247153 | A1 | 10/2007 | Yu |
| 2008/0012563 | A1 | 1/2008 | Weiss et al. |
| 2008/0150532 | A1 | 6/2008 | Slavin et al. |
| 2010/0198050 | A1 | 8/2010 | Mori |
| 2010/0241012 | A1 | 9/2010 | Yin et al. |
| 2011/0028828 | A1 | 2/2011 | Daye et al. |
| 2011/0181285 | A1* | 7/2011 | Greiser ............. A61B 5/055 324/309 |
| 2013/0248533 | A1 | 9/2013 | Wallis et al. |
| 2014/0296702 | A1* | 10/2014 | Griswold ............ A61B 5/4244 600/416 |
| 2014/0330106 | A1 | 11/2014 | Banerjee et al. |

FOREIGN PATENT DOCUMENTS

| | | |
|---|---|---|
| GB | 2513474 | 10/2014 |
| GB | 2524587 | 9/2015 |
| WO | WO 2006134430 | 12/2006 |
| WO | 2008144391 A1 | 11/2008 |
| WO | WO 2008/144391 | 11/2008 |
| WO | 20130046158 | 4/2013 |
| WO | WO 2013/046158 | 4/2013 |
| WO | 20130088149 | 6/2013 |
| WO | 20130088151 | 6/2013 |
| WO | WO 2013/088149 | 6/2013 |
| WO | 20140011925 | 1/2014 |
| WO | 20140140635 | 9/2014 |
| WO | 20150155521 | 10/2015 |
| WO | WO 2015/144916 | 10/2015 |

OTHER PUBLICATIONS

Bydder et al., Assessment of Liver Fat Quantification in the Presence of Iron, Magn Reson Imaging. Jul. 2010 ; 28(6): 767-776.*
Messroghli eat al., Modified Look-Locker Inversion Recovery (MOLLI) for High-ResolutionT1Mapping of the Heart, Magnetic Resonance in Medicine 52:141-146, 2004.*
van Werven et al. Assessment of Hepatic Steatosis in Patients Undergoing Liver Resection: Comparison of US, CT, T1-weighted Dual-Echo MR Imaging,and Point-resolved 1 H MR Spectroscopy, Radiology: vol. 256: No. 1—Jul. 2010.
McPherson et al. Magnetic resonance imaging and spectroscopy accurately estimate the severity of steatosis provided the stage of fibrosis is considered. Journal of Hepatology, vol. 51, Issue 2, Aug. 2009, pp. 389-397.
RM SSE, http://www.uta.edu/faculty/sawasthi/Statistics/glosr.html Nov. 2007.
Aisen, et al. Detection of liver fibrosis with magnetic cross-relaxation. Magn Reson Med. 1994; 31:551-6).
Alanen et al., Acta. Radiol., Jul. 1998; 39 (4): 434-9. "MR and magnetisation transfer imaging in cirrhotic and fatty livers."
Bacic et al. NMR study of water exchange across the hepatocyte membrane. Magn Reson Imaging 1989; 7:411-416.
Banerjee et al "Multiparametric Magnetic Resonance for the non-invasive diagnosis of liver disease." J Hepatol. (2014) 60(1):69-77.
Bohte, A. E., A. de Niet, et al. "Non-invasive evaluation of liver fibrosis: a comparison of ultrasound-based transient elastography and MR elastography in patients with viral hepatitis B and C." Eur Radiol 24(3): 638-48. Oct. 2013.
Bosch, J., J. G. Abraldes, et al. (2009). "The clinical use of HVPG measurements in chronic liver disease." Nat Rev Gastroenterol Hepatol 6(10): 573-582.
Bravo, A. A.,et al. (2001). "Liver Biopsy." New England Journal of Medicine 344(7): 495-500.
Bredella MA, et al J Comput Assist Tomogr. May-Jun. 2010;34(3):372-6. Breath-hold 1H-magnetic resonance spectroscopy for intrahepatic lipid quantification at 3 Tesla.
British Liver Trust, 2006 Alcohol and liver disease. Ringwood: British Liver Trust, 2006.
Chamuleau, et al. Is the magnetic resonance imaging proton spin-lattice relaxation time a reliable noninvasive parameter of developing liver fibrosis? Hepatology. 1988; 8:217-21.
Cheng J. Magnetic Resonance Imaging (2012) 36(4): 805-824.
Colecchia A, et al Measurement of spleen stiffness to evaluate portal hypertension and the presence of esophageal varices in patients with HCV-related cirrhosis. Gastroenterology. Sep. 2012;143(3):646-54.
Ekstedt M, et al. Hepatology 2006; 44: 865. Long-term follow-up of patients with NAFLD and elevated liver enzymes.
El Badry AM et al, Annals of Surgery 250(5), Nov. 2009, 691-697. Assessment of Hepatic Steatosis by Expert Pathologists: The End of a Gold Standard.
Ferreira VM, et al Non-contrast T1-mapping detects acute myocardial edema with high diagnostic accuracy: a comparison to T2-weighted cardiovascular magnetic resonance .J Cardiovasc Magn Reson 2012;14:42.
Fleming, Kate M., et al. "Abnormal liver tests in people aged 75 and above: prevalence and association with mortality." Alimentary pharmacology & therapeutics 34.3 (2011): 324-334.
Ghugre and Wood Relaxivity-iron calibration in hepatic iron overload: probing underlying biophysical mechanisms using a Monte Carlo model. Magn Reson Med 2011; 65:837-847.
Ghugre et al. Multi-field behavior of Relaxivity in an Iron-rich environment. Proc Intl Soc Mag Reson Med. 2008; 16:644).
Ghugre et al., Mechanisms of tissue-iron relaxivity: nuclear magnetic resonance studies of human liver biopsy specimens. Magn Reson Med. 2005; 54:1185-93.
Goldberg, et al. Hepatic cirrhosis: magnetic resonance imaging. Radiology. 1984; 153:737-9.
Graham and Henkelman Understanding pulsed magnetisation transfer. J Magn Reson Imaging 1997; 7:903-912.
Guo H. et al., J Magn Reson Imaging, Aug. 2009; 30(2):394-400. Myocardial T2 Quantitation in Patients With Iron Overload at 3 Tesla.
Henninger, et al. Evaluation of MR imaging with T1 and T2 mapping for the determination of hepatic iron overload. Eur Radiol. 2012; 22:2478-86.

(56) References Cited

OTHER PUBLICATIONS

Heye, et al. MR relaxometry of the liver: significant elevation of T1 relaxation time in patients with liver cirrhosis. Eur Radiol. 2012; 22:1224-32.
Hilt PJ Thesis, Quantification of Cardiac Longitudinal Relaxation (T1) at 3.0 T During Normal and Hyperoxic Breathing Conditions, Aug. 2008.
Hines CDG et al. Radiology; 254: 1; Jan. 2010 Quantification of Hepatic Steatosis with 3T MR Imaging: Validation in ob/ob Mice.
Ishak et al., Histological grading and staging of chronic hepatitis. J Hepatol. 1995; 22:696-9.
Janiec DJ et al, Obes Surg. Apr. 2005;15(4):497-501. Histologic variation of grade and stage of non-alcoholic fatty liver disease in liver biopsies.
Keevil, et al. Non-invasive assessment of diffuse liver disease by in vivo measurement of proton nuclear magnetic resonance relaxation times at 0.08 T. Br J Radiol. 1994; 67:1084-1087).
Kim, et al. Quantitative evaluation of liver cirrhosis using T1 relaxation time with 3 tesla MRI before and after oxygen inhalation. J Magn Reson Imaging. 2012; 36:405-10.
Klasen J, et al Diffusion-weighted imaging (DWI) of the spleen in patients with liver cirrhosis and portal hypertension. Magn Reson Imaging. Sep. 2013;31(7):1092-6.
Li Zhou et al Plos One (2013) 8(12): e83697.
Mackay A et al Magnetic Resonance in Medicine (1994) 32(6): 673-677.
Merkel, C. and S. Montagnese "Hepatic venous pressure gradient measurement in clinical hepatology." Digestive and Liver Disease 43(10): 762-767.
Messroghli DR et al, 2007 Optimization and Validation of a Fully-Integrated Pulse Sequence for Modified Look-Locker Inversion-Recovery (MOLLI) T1 Mapping of the Heart, Journal of Magnetic Resonance Imaging 26:1081-1086, 2007.
Messroghli DR, et al, 2004 Magn Reson Med 2004; 52:141-146. Modified Look-Locker inversion recovery (MOLLI) for high-resolution T1 mapping of the heart.
Nedredal GI et al Portal hypertension correlates with splenic stiffness as measured with MR elastography. J Magn Reson Imaging. Jul. 2011;34(1):79-87.
Patch, D., et al. (1999). "Single portal pressure measurement predicts survival in cirrhotic patients with recent bleeding." Gut 44(2): 264-9.
Perello A, et al (1999). "Wedged hepatic venous pressure adequately reflects portal pressure in hepatitis C virus-related cirrhosis." Hepatology 30(6): 1393-1397.
Piechnik SK, et al, 2010 J Cardiovasc Magn Reson. Nov. 19, 2010;12:69. Shortened Modified Look-Locker Inversion recovery (ShMOLLI) for clinical myocardial T1-mapping at 1.5 and 3 T within a 9 heartbeat breathhold.
Piechnik SK et al, 2013 "Normal variation of magnetic resonance T1 relaxation times in the human population at 1.5 T using ShMOLLI." J Cardiovasc Magn Reson 15: 13.
Regev A et al, Am J Gastroenterol. Oct. 2002; 97(10):2614-8. Sampling error and intra-observer variation in liver biopsy in patients with chronic HCV infection.
Rincon D et al. (2007). "Prognostic value of hepatic venous pressure gradient for in-hospital mortality of patients with severe acute alcoholic hepatitis." Aliment Pharmacol Ther 25(7): 841-8.
Ripoll C et al. (2005). "Influence of hepatic venous pressure gradient on the prediction of survival of patients with cirrhosis in the MELD Era." Hepatology 42(4): 793-801.
Rohrer et al., Comparison of magnetic properties of MRI contrast media solutions at different magnetic field strengths. Invest Radiol. 2005; 40:715-24.
St Pierre, et al. Noninvasive measurement and imaging of liver iron concentrations using proton magnetic resonance. Blood. 2005; 105:855-61.
Standish RA et al Gut. Apr. 2006;55(4):569-78. An appraisal of the histopathological assessment of liver fibrosis.

Thomsen, et al. Prolonged T1 in patients with liver cirrhosis: An in vivo MRI study. Magn Reson Imaging. 1990; 8:599-604.
Varghese T et al. "Elastographic imaging using a handheld compressor." Ultrason Imaging. Jan. 2002;24(1):25-35.
Versluis et al., Detection of cerebral microbleeds: Physical principles, technical aspects and new developments. In: Cerebral Microbleeds ed. Werring DJ. Cambridge University Press, 2011; pp. 13-21.
Vymazal et al., 1992 T1 and T2 of ferritin at different field strengths: Effect on MRI. Magn Reson Med. 1992; 27:367-74.
Vymazal et al. 1996 The relation between brain iron and NMR relaxation times: An in vitro study. Magn Reson Med. 1996; 35:56-61.
Wood, et al. MRI R2 and R2 mapping accurately estimates hepatic iron concentration in transfusion-dependent thalassemia and sickle cell disease patients. Blood. 2005; 106:1460-5).
Clinical NMR Group. "Magnetic resonance imaging of parenchymal liver disease: a comparison with ultrasound, radionuclide scintigraphy and X-ray computed tomography." Clinical Radiology 38.5 (1987): 495-502.
Koenig, Seymour H., and Rodney D. Brown. "Relaxometry of tissue." Encyclopedia of Magnetic Resonance, (2007): 1-13.
International Search Report Application No. PCT/GB2012/053116 dated May 6, 2013, 12 pages.
GB Search Report Application No. GB1121404.6 dated Apr. 30, 2012, 3 pages.
Magnetic Resonance Imaging Clinics of North America, "MR. Imaging of Diffuse Liver Disease (Hepatic Fat and Iron)", Siegelman E S, vol. 5, May 1997, pp. 347-365.
Bieri and Scheffler, Fundamentals of balanced steady state free precession MRI, Journal of magnetic resonance imaging, 38, 2-11, 2013.
Burt et al, Myocardial T1 mapping: techniques and potential applications, Cardiac imaging, 34(2), 377-395, 2014.
Chundru et al, MRI of diffuse liver disease: the common and uncommon etiologies, diagnostic and interventional radiology, 2013.
De Miguel M H et al, "Evaluation of quantitative magnetic resonance imaging as a noninvasive technique for measuring renal scarring in a rabbit model of antiglomerular basement membrane disease.", Journal of the American Society of Nephrology : JASN May 1994, (May 1994), vol. 4, No. 11, pp. 1861-1868.
Fischer R et al. "Assessment of iron stores in children with transfusion siderosis by biomagnetic liver susceptometry", Hematology 1999;60(4):289-299.
Hamilton et al "Effect of PRESS and STEAM sequences on magnetic resonance spectroscopic liver fat quantification", J. Magn. Reson. Imaging 2009; 30:145-152.
Hamilton G, Middleton MS, Hooker JC, Haufe WM, Forbang NI, Allison MA, et al. In vivo breath-hold (1) H MRS simultaneous estimation of liver proton density fat fraction, and T1 and T2 of water and fat, with a multi-TR, multi-TE sequence. J Magn Reson Imaging [Internet]. Jun. 25, 2015 [cited Nov. 19, 2015];42(6):1538-43.
Hamilton G, Yokoo T, Bydder M, Cruite I, Schroeder ME, Sirlin CB, et al In vivo characterization of the liver fat 1H MR spectrum. NMR Biomed. 2011;24(7):784-90.
Hargreaves, Rapid Gradient-Echo Imaging, Journal of Magnetic Resonance Imaging, 36, 1300-1313, 2012.
Hines CDG, Yu H, Shimakawa A, McKenzie CA, Brittain JH, Reeder SB, T1 independent, T2 corrected MRI with accurate spectral modeling for quantification of fat: Validation in a fat-water-Spio phantom. J Magn Reson Imaging. 2009;30(5):1215-22.
Idilman IS et al., "Hepatic steatosis: quantification by proton density fat fraction with MR imaging versus liver biopsy" Radiology 2013;267:767-775.
Kellman et al., J. Cardiovascular Mag. resonance (2015) 17:3.
Kellman P. et al., "Influence of Off-resonance in myocardial T1-mapping using SSFP based MOLLI method", J. Cardiovasc. Magn. Reson. Jul. 22, 2013;15:63.
Kim et al, Myocardial T1 and T2 mapping: techniques and clinical applications, Korean journal of radiology, 18(1), 113-131, 2017.

(56) References Cited

OTHER PUBLICATIONS

Larmour et al., "Characterization of T1 bias in skeletal muscle from fat in MOLLI and SASHA pulse sequences: Quantitative Fat-Fraction imaging with T1 mapping", Magnetic Resonance in Medicine 77:237-249 (2017).
Ling C R et al., "Changes in NMR relaxation time associated with local inflammatory response", Physics in Medicine and Biology, Institute of Physics Publishing, Bristol GB, (Jun. 1, 1982), vol. 27, No. 6, pp. 853-860.
Ma et al, Magnetic Resonance Fingerprinting, Nature, 495, 187-193, 2013.
Mozes FE, et al., "Influence of fat on liver T1 measurements using modified Look-Locker inversion recovery (MOLLI) methods at 3T", J. Magn. Reson. Imaging. Jan. 13, 2016; 44:105-111.
Sahani The Oncologist (2004):9:385-397.
Sirlin C et al., "Magnetic Resonance Imaging Quantification of Liver Iron", Magn. Reson. Imaging Clin. N. Am. 2012;18(3):359.
Squires et al., J Pediatr. May 2006;148(5):652-658).
Storey P et al., "R2 imaging of transfusional iron burden at 3T and comparison with 1.5T", J. Magn. Reson. Imaging 2007;25:540-547).
Szczepaniak LS et al., "Magnetic resonance spectroscopy to measure hepatic triglyceride content: prevalence of hepatic steatosis in the general population", Am. J. of Physiol. Endocrinol. Metab. 2005;288:E462-468.
Tang A et al. "Nonalcoholic Fatty Liver Disease: MR Imaging of Liver Proton Density Fat Fraction to Assess Hepatic Steatosis", Radiology 2013;267:422-431.
Tunnicliffe EM, Banerjee R, Pavlides M, Neubauer S, Robson MD., A model for hepatic fibrosis: the competing effects of cell loss and iron on shortened modified Look-Locker inversion recovery T 1 (shMOLLI- T 1) in the liver. J Magn Reson Imaging [Internet]. Jul. 2016 [cited Sep. 16, 2016].
Wang et al, Factors influencing flip angle mapping in mri: rf pulse shape, slice-select gradients, off-resonance excitation, and bo inhomogeneities, magnetic resonance in medicine, 56, 463-468, 2006.
Wood J, "Impact of Iron Assessment by MRI", AHS Education Book, Dec. 10, 2011; 1:443-450.
Yu H, McKenzie CA, Shimakawa A, Vu AT, Brau ACS, Beatty PJ, et al., Multiecho reconstruction for simultaneous water-fat decomposition and T2 estimation. J Magn Reson Imaging [Internet]. Oct. 2007 [cited Mar. 5, 2015];26 (4):1153-61.
United Kingdom Office Action for Application No. GB1222449.9 dated Jun. 15, 2016.
United Kingdom Office Action for Application No. GB1222449.9 dated May 20, 2016.
United Kingdom Office Action for Application No. GB1222449.9 dated Jul. 25, 2016.
United Kingdom Office Action for Application No. GB1222449.9 dated May 7, 2013.
Combined Search and Examination Report for Application No. GB1222449.9, dated May 7, 2013, pp. 1-39.
Examination Report for Application No. GB1222449.9, dated May 20, 2016, pp. 1-7.
Examination Report for Application No. GB1222449.9, dated Jun. 15 2016, pp. 1-4.
Examination Report for Application No. GB1222449.9, dated Jul. 25 2016, pp. 1-3.
Sahani, Dushyant and Sanjeeva P. Kalva, "Imaging the Liver", The Oncologist, 2004, pp. 385-397, vol. 9.
Mescam, Muriel, et al., "Coupling texture analysis and physiological modeling for liver dynamic MRI interpretation", Proceedings of the 29th Annual International Conference of the IEEE EMBS, Lyon, France, 2007, pp. 4223-4226, vol. SaA06.3.
Mescam, Muriel, et al., "Multiscale Model of Liver DCE-MRI Towards a Better Understanding of Tumor Complexity", IEEE Transactions on Medical Imaging, 2010, pp. 699-707, vol. 29, No. 3, doi: 10.1109/TMI.2009.2031435.
Sommer, Wieland H., et al., "Contrast agents as a biological marker in magnetic resonance imaging of the liver: conventional and new approaches" Abdominal Imaging, 2012, pp. 164-179, vol. 37, doi: 10.1007/s00261-011-9734-9.
Thng, Choon Hua, et al., "Perfusion magnetic resonance imaging of the liver", World Journal of Gastroenterology, 2010, pp. 1598-1609, vol. 16, No. 13, doi: 10.3748/wjg.v16.i13.1598.
Kumar, Ashish, et al., "Hepatic venous pressure gradient measurement: Time to learn!", Indian Journal of Gastroenterology, 2008, pp. 74-80, vol. 27, No. 2, http://indianjgastro.com/IJG_pdf/march2008/march08_pg74-80.pdf.
Do, Richard K.G., et al., "Diagnosis of Liver Fibrosis and Cirrhosis with Diffusion-Weighted Imaging: Value of Normalized Apparent Diffusion Coefficient Using the Spleen as Reference Organ", American Journal of Roentgenology, 2010, pp. 671-676, vol. 195, doi: 10.2214/AJR.09.3448.
De Miguel, Mariano H., et al., "Evaluation of Quantitative Magnetic Resonance Imaging as a Noninvasive Technique for Measuring Renal Scarring in a Rabbit Model of Antiglomerular Basement Membrane Disease", Journal of the American Society of Nephrology, 1994, pp. 1861-1868, vol. 4.
Ling, C Rosemary and Margaret A. Foster, "Changes in NMR relaxation time associated with local inflammatory response", Physics in Medicine & Biology, 1982, pp. 853-860, vol. 27, No. 6, Great Britain.
Squires, Robert H., et al., "Acute Liver Failure in Children: The First 348 Patients in the Pediatric Acute Liver Failure Study Group", The Journal of Pediatrics, 2006, pp. 652-658, vol. 148, No. 5, doi: 10.1016/j.jpeds.2005.12.051.

\* cited by examiner

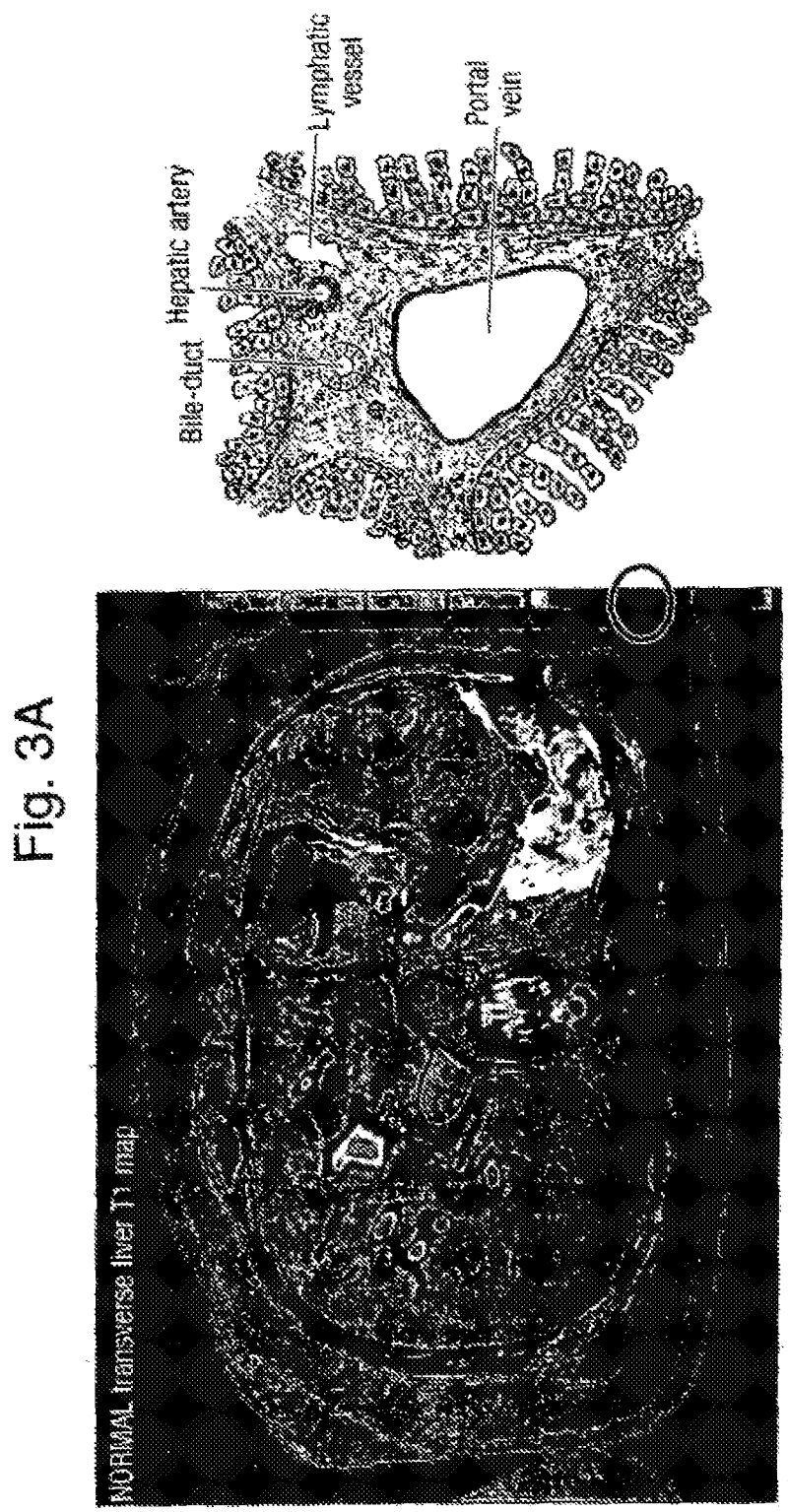

Case 1

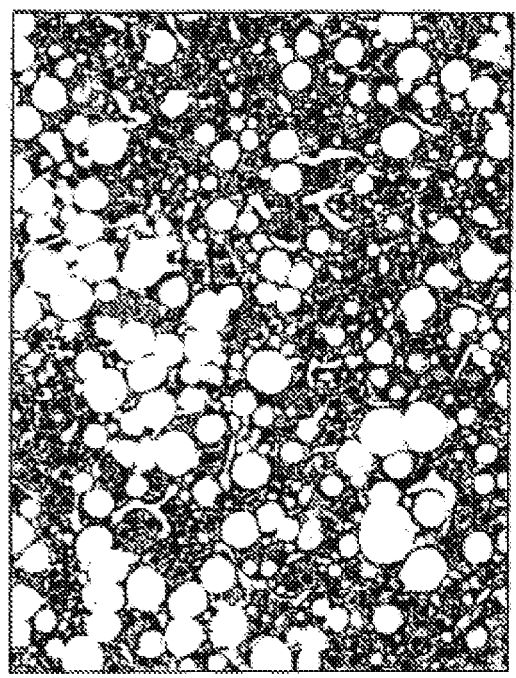
Fig. 6

Fig. 8A
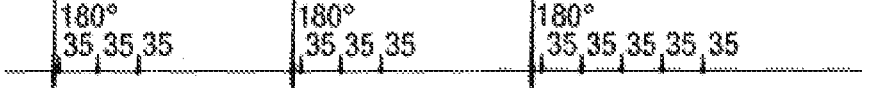
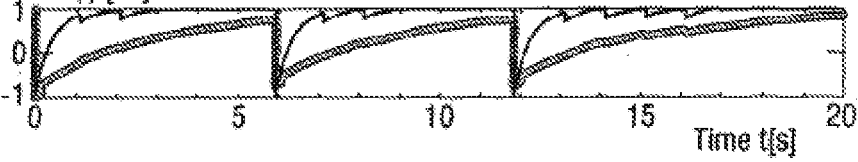
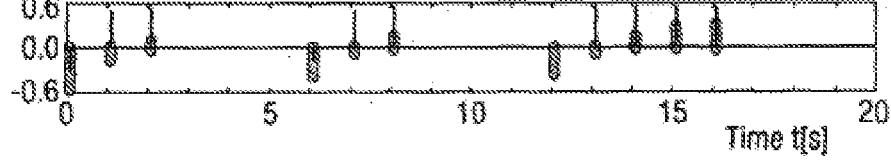
Fig. 8B
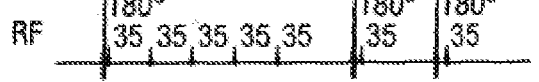
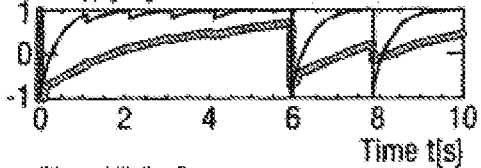
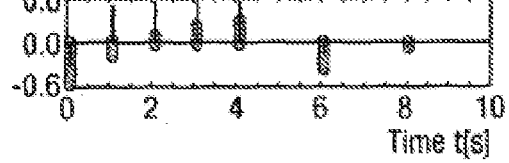

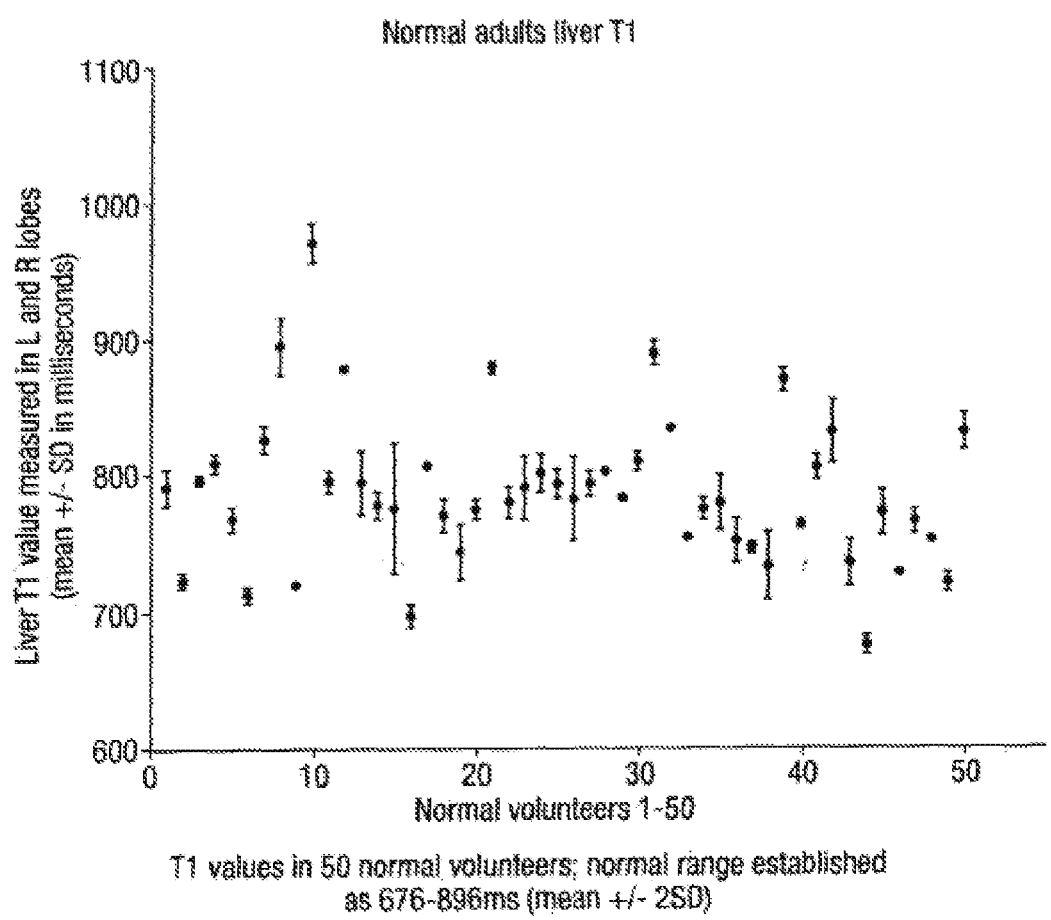

Hepatic Lipid Content in 100 volunteers

HLC measured in 100 normal volunteers, BMI 18-30kg/m$^2$,: normal range established as 0-4.7%, with median 0.75% and interquartile range 0.47-1.25%

ROC of normals + ISHAK 0-2 versus ISHAK > 2

Fig. 21

| Appearance | Ishak stage: Categorical description | Ishak stage: Categorical assignment | Fibrosis measurement* |
|---|---|---|---|
| 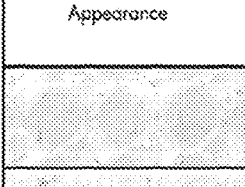 | No fibrosis (normal) | 0 | 1.9% |
|  | Fibrous expansion of some portal areas ± short fibrous septa | 1 | 3.0% |
|  | Fibrous expansion of most portal areas ± short fibrous septa | 2 | 3.6% |
|  | Fibrous expansion of most portal areas with occasional portal to portal (P-P) bridging | 3 | 6.5% |
|  | Fibrous expansion of portal areas with marked bridging (portal to portal (P-P) as well as portal to central (P-C)) | 4 | 13.7% |
|  | Marked bridging (P-P and/or P-C), with occasional nodules (incomplete cirrhosis) | 5 | 24.3% |
|  | Cirrhosis, probable or definite | 6 | 27.8% |

MULTI-PARAMETRIC MAGNETIC RESONANCE DIAGNOSIS AND STAGING OF LIVER DISEASE

CROSS-REFERENCE TO RELATED APPLICATIONS

This application is the National Stage of International Application No. PCT/GB2012/053116, filed 13 Dec. 2012, which claims the benefit of and priority to GB application 1121404.6, filed 13 Dec. 2011 and U.S. provisional application 61/630,508, filed 13 Dec. 2011, having the title "MULTI-PARAMETRIC MAGNETIC RESONANCE DIAGNOSIS & STAGING OF LIVER DISEASE", the contents of all of which are incorporated by reference as if fully set forth herein.

TECHNICAL FIELD

The present disclosure generally relates to medical imaging and, more particularly, relates to systems and methods for performing multi-parametric magnetic resonance diagnosis and staging of liver disease.

BACKGROUND

As many as one in ten adults in the UK have some form of liver disease (British Liver Trust. Alcohol and liver disease. Ringwood: British Liver Trust, 2006). Liver disease is currently the fifth most common cause of mortality for both men and women (Department of Health. Quality Strategy Team Report on Liver Disease: A scoping study into the nature and burden of the disease, 2006). However, whilst the mortality rates for the other four major causes of death are falling, the trend for liver disease is rising in both sexes at an alarming rate there has been a five-fold increase in the prevalence of liver cirrhosis in the last 30 years. The current childhood obesity epidemic, increasing alcohol misuse and viral hepatitis are all contributing to this. Moreover, non-alcoholic fatty liver disease (NAFLD) doubles the risk of cardiovascular mortality (Long-term follow-up of patients with NAFLD and elevated liver enzymes. Ekstedt M, et al. Hepatology 2006; 44: 865).

The problem with liver disease is that often symptoms of the disease are not apparent until the disease reaches an advanced stage. Thus, there is a pressing need for a reliable diagnostic tool for liver disease to identify early disease and target therapies to those patients that may benefit (e.g., antiviral therapy in progressive hepatitis C, weight reduction surgery in fatty liver disease).

The current accepted practice, or "gold standard", for diagnosing liver disease is an ultrasound-guided liver biopsy. This is less than ideal as there is a small but significant complication risk (1:1000 of severe bleeding, especially in coagulopathic patients). Furthermore, only 0.002% of the liver is examined, and there is great intra and inter-observer variability in histological interpretation (see, e.g., Sampling error and intra-observer variation in liver biopsy in patients with chronic HCV infection. Regev A et al, Am J Gastroenterol. 2002 October; 97(10):2614-8. Histologic variation of grade and stage of non-alcoholic fatty liver disease in liver biopsies. Janiec D J et al, Obes Surg. 2005 April; 15(4):497-501. Assessment of Hepatic Steatosis by Expert Pathologists: The End of a Gold Standard. El Badry A M et al, Annals of Surgery 250(5), November 2009, 691-697).

There are few non-invasive diagnostic alternatives for liver disease. Ultrasonography is not specific, is not sensitive in early disease, and is of limited efficacy in obese patients. Transcutaneous elastography can aid in quantifying fibrosis, but is also of limited use in large patients due to reduced acoustic windows. Magnetic resonance (MR) elastography is superior, but expensive, operator dependant and not disease specific.

There are currently no clinical magnetic resonance (MR) protocols for the diagnosis of parenchymal liver disease. Previously published studies have concluded, for example, that there is no justification for the use of proton nuclear magnetic resonance imaging techniques or the in vivo measurement of hepatic T1 relaxation time. ("MRI of parenchymal liver disease.", Clin. Radiol. 1987 sep; 38 (5): 495-502; Aisen et al., "Detection of liver fibrosis with magnetic cross-relaxation.", Magn. Reson. Med. 1994 May; 31 (5): 551-6; Alanen et al., "MR and magnetisation transfer imaging in cirrhotic and fatty livers." Acta. Radiol., 1998 July; 39 (4): 434-9). For a clinically useful tool, further refinement in MR imaging to assess parenchymal tissue fibrosis has been desired to allow differentiation between NAFLD, which is relatively benign, and non-alcoholic steatohepatitis (NASH), which has a worse prognosis and is more strongly linked to coronary artery disease.

Several murine models of liver disease have shown that metabolic dysregulation can lead to steatosis and fibrosis. These include genetic models (e.g., leptin-deficient mouse) and diet-manipulated models (e.g., choline deficient mouse, Western high fat diet mouse). Promisingly, quantitative MR imaging & spectroscopic analysis of liver fat have been validated against post-mortem studies in these models (Quantification of Hepatic Steatosis with 3T MR Imaging: Validation in ob/ob Mice. Hines C D G et al. Radiology; 254: 1; January 2010). However, the phenotypes of these models do not match the human mix of persistent exposure to obesogenic environmental factors (e.g., snacking, sedentary behaviours), chronic Western diet, toxin exposure (alcohol) and slowly progressive fibrosis.

Accordingly, there is a need to address the aforementioned deficiencies and inadequacies.

SUMMARY

Briefly described, systems and methods for performing multi-parametric magnetic resonance (MR) diagnosis for liver disease are provided.

In magnetic resonance (MR) imaging, tissue contrast is generated by a combination of intrinsic tissue properties such as spin-lattice (T1) and spin-spin (T2) relaxation times, and extrinsic properties such as imaging strategies and settings. Signal intensity in conventional MR images is displayed on an arbitrary scale, and thus is not adequate for direct comparisons. T1 relaxation times depend on the composition of tissues. T1 relaxation times exhibit characteristic ranges of normal values at a selected magnetic field strength. Deviation from established ranges can thus be used to quantify the effects of pathological processes.

We have discovered that T1 mapping of the liver can reliably show differences in extracellular fluid (ECF) content and thereby allow quantification of the degree of liver fibrosis and thus serve as a biomarker for liver disease. In particular, T1 mapping in conjunction with concurrent interpretation of lipid and iron content provides robust, rapid non-invasive diagnosis of the type and/or severity of many common liver diseases, such as NAFLD/NASH, hepatitis, and iron overload.

One embodiment of the present systems and methods comprises: positioning a subject, for example a patient, in association with a medical imaging device, preferably a magnetic resonance (MR) scanner; using the medical imaging device to measure the subject's liver for extracellular fluid; measuring the liver for iron content, in particular for iron overload; determining whether iron overload may be indicated or present from the measurement for iron content, and if indicated correcting the measurement for extra cellular fluid; measuring the liver for hepatic lipid content (HLC); and determining from said measurements the presence or absence of liver disease.

Another embodiment is a system comprising a medical imaging device, preferably a magnetic resonance (MR) scanner, at least one computing device and at least one application executable in the at least one computing device, the at least one application comprising logic by which the present system and/or method measures a subject's liver for extracellular fluid; measures the liver for iron content, in particular for iron overload; determines whether iron overload may be indicated or present from the measurement for iron content, and if indicated corrects the measurement for extra cellular fluid; measures the liver for hepatic lipid content (HLC); and determines from said measurements the presence or absence of liver disease.

In any one or more of the embodiments, the subject's liver can be measured for extracellular fluid using a magnetic resonance (MR) scanner. The liver can also be measured for iron content and/or hepatic lipid content using an MR scanner. In particular, the subject's liver can be measured for extracellular fluid using T1 mapping, iron content measured using T2* imaging and hepatic lipid content measured using MR spectroscopy, for example, $^1$H MR spectroscopy.

In any one or more of the embodiments, the subject's liver can also be measured for iron content using one or more of T2 mapping, measuring one or more blood biomarkers, such as ferritin, transferrin, transferrin saturation, hepcidin, soluble transferrin receptor (sTfR) index (sTfR/log ferritin), or MR spectroscopy. For example, the width of the $^1$H MRS spectra can indicate higher than normal iron loads.

In any one or more of the embodiments, the subject's liver can also be measured for hepatic lipid content (HLC) using one or more of using one or more of Dixon in and out of phase imaging, or dual-echo techniques.

In any one or more of the embodiments the spin-lattice T1 mapping can be performed using repeated inversion recovery (IR) experiments. For example, a modified Look Locker inversion (MOLLI) recovery pulse sequence. In one or more further embodiments, among others, where a shortened breath-hold is desired, the spin-lattice (T1) mapping can be performed using a shortened modified Look Locker inversion recovery (Sh-MOLLI) sequence comprising performing consecutive inversion-recovery (IR) experiments that include front-loaded sampling followed by one or more subsequent samples and conditionally including the subsequent one or more samples for the T1 mapping based on empirical relationships between the estimated spin-lattice relaxation time T1, heart rate, heart beat period or experimentally achieved relaxation recovery times or degrees, and estimated fit error associated with the subsequent experiments and samples.

In any one or more embodiments the spin-lattice (T1) mapping can be performed using consecutive inversion-recovery (IR) experiments, wherein the consecutive IR experiments comprise a first IR experiment, a second IR experiment, and a third IR experiment, the first IR experiment comprising a number of samples exceeding a number of samples of both the second IR experiment and the third IR experiment. The method further comprises conditionally processing the samples in the first, second, and third IR experiments.

The measurement for liver disease by any one or more of the aforementioned embodiments can determine, for example, the presence of one or more of non-alcoholic fatty liver disease (NAFLD), non-alcoholic steatohepatitis (NASH), high hepatic lipid content (HLC), hepatic fibrosis, a disease associated with hepatic fibrosis, hepatitis, or a condition associated with iron overload. As further examples, the measurement can determine the presence of any one or more of the following diseases: Autoimmune hepatitis, primary biliary cirrhosis, primary sclerosing cholangitis, viral hepatitis, chronic hepatitis, drug-induced hepatitis, haemochromatosis, thallassaemia, alcoholic hepatitis, alcoholic liver cirrhosis, portal hypertension, vascular liver disease, idiopathic hepatic fibrosis, sarcoidosis, hepatic cysts, and hemangiomas.

Other systems, methods, features, and advantages of the present disclosure for performing multi-parametric diagnosis of a liver will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

The patent or application file may contain at least one drawing executed in color. Copies of this patent or patent application publication with color drawing(s) will be provided by the Office upon request and payment of the necessary fee.

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3A is a transverse liver T1 map of a normal liver and FIG. 3B is a transverse liver T1 map of an essentially normal liver with mild steatosis.

FIG. 6 shows a biopsy of the liver of FIG. 5 confirming the presence of NASH.

FIGS. 8A-B show a side-by-side simulated comparison of ECG-gated pulse sequence schemes for simulation of a) MOLLI and b) Sh-MOLLI at a heart rate of 60 bpm for T1 mapping of the liver.

FIG. 12 shows T1 values in 50 normal volunteers.

FIG. 21 depicts the differences between morphological appearance, description, stage scoring and liver fibrosis measurement are reported by Standish R. et al (An appraisal of the histopathological assessment of liver fibrosis. Standish R A, Cholongitas E, Dhillon A, Burroughs A K, Dhillon A P Gut. 2006 April; 55(4):569-78.

DETAILED DESCRIPTION

Figure 1:
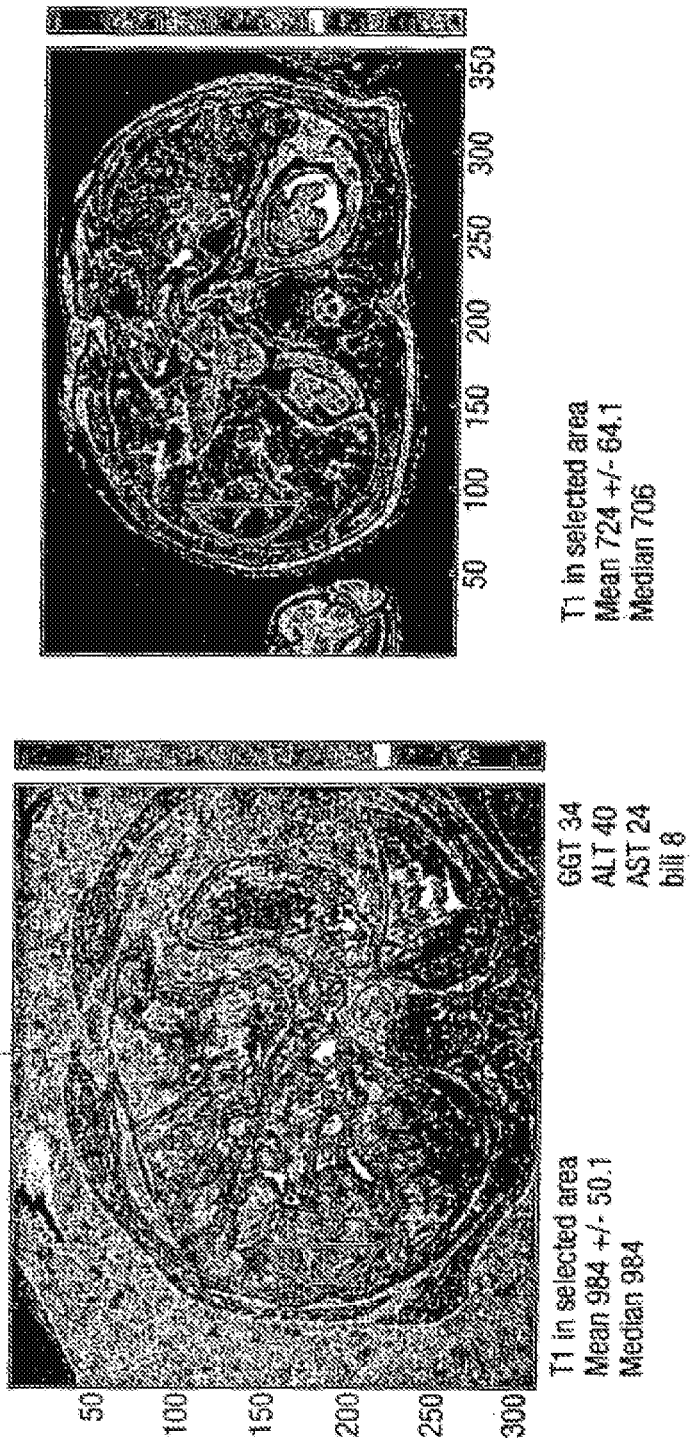
FIG. 1 presents a comparison of transverse liver T1 maps of normal liver to transverse liver T1 maps of liver having elevated extracellular fluid.

Having summarized various aspects of the present disclosure, reference will now be made in detail to the description of the disclosure as illustrated in the drawings. While the disclosure will be described in connection with these drawings, there is no intent to limit it to the embodiment or embodiments disclosed herein. On the contrary, the intent is to cover all alternatives, modifications and equivalents included within the spirit and scope of the disclosure as defined by the appended claims.

Medical imaging, for example magnetic resonance (MR) imaging, can be used to measure tissue characteristics that can in combination help to determine the presence and severity of liver disease. These parameters include liver fibrosis, liver iron content and liver fat content (aka, hepatic lipid content (HLC))).

T1 mapping of the liver can reliably show differences in extracellular fluid (ECF) content. Higher T1 relaxation time resulting from T1 mapping of the liver for extracellular fluid measurement is an indication of fibrosis in the liver. A higher T1 relaxation time can indicate a higher degree of hepatic fibrosis or active hepatitis. Magnetic resonance (MR) spectroscopy, for example, can accurately measure the lipid: water ratio within a volume of interest (voxel), and a high ratio represents high hepatic lipid content (HLC). Elevated HLC is characteristic of Fatty Liver Disease (FLD). In 20% of FLD patients, there is coexistent chronic liver inflammation due to steatohepatitis. This can be diagnosed by an elevated HLC and an elevated T1 value.

We have discovered, however, that elevated liver iron, or iron overload, can alter the T1 relaxation time. Mild iron overload is relatively common in the general population, and higher still in patients with suspected liver disease. The most important causes of iron overload are hereditary hemochromatosis (HHC), a highly prevalent genetic disease with autosomal dominant heritability, transfusion iron overload, and chronic liver disease. Iron overload tends to lower T1 relaxation time and, thereby, cause the measured T1 relaxation time to underreport, for example, extracellular fluid measurement. Iron overload commonly causes liver cirrhosis if left untreated, so the two commonly coexist.

We have found, therefore, that the combination of liver T1 mapping for extracellular fluid measurement, measurement for hepatic lipid content, and measurement for iron content, for example iron overload, allows for rapid and accurate assessment of a liver for the presence of liver disease. Measuring for iron content allows for a determination whether a correction should be applied to measured T1 values, thus, correcting for underreporting by T1 values when iron overload is present.

We observed in a study that liver T1 values from transverse liver T1 maps were elevated in some patients, in particular obese patients, showing a relationship between T1 values and the presence of extracellular fluid and liver fibrosis. High T1 values correlated with the presence of high extracellular fluid and liver fibrosis. See e.g., FIG. 1.

Figure 2:
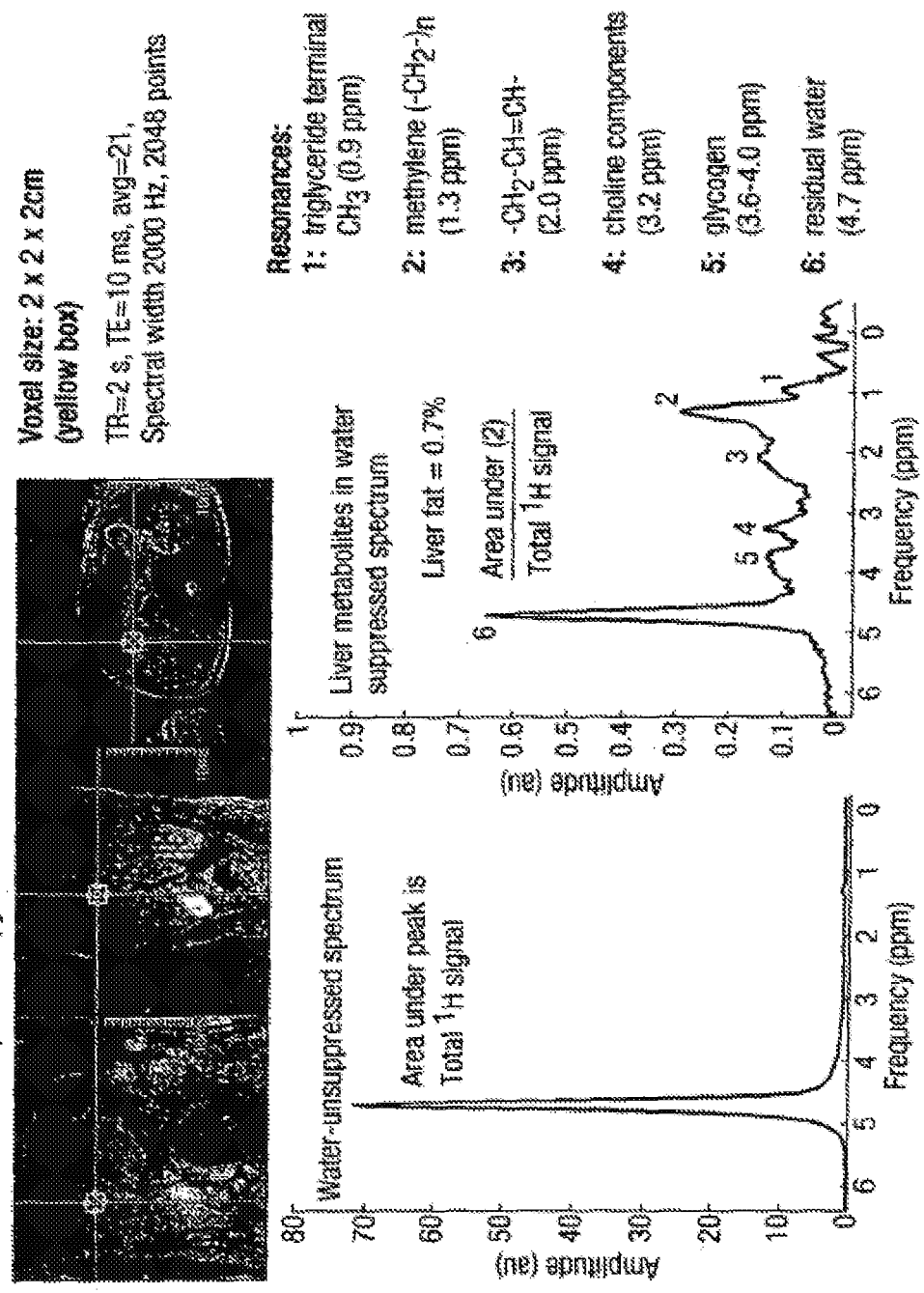
FIG. 2 illustrates use of MR spectroscopy to measure hepatic liver content (HLC).

High extracellular fluid can also be the result, however, of high hepatic lipid content (HLC) (also referred to as "liver fat"). MR spectroscopy can be used to measure liver fat (See e.g., FIG. 2), for example rapid $^1$H MR spectroscopy. Other methods that can be used, however, to measure HLC include Dixon in and out of phase imaging and dual-echo techniques (Assessment of Hepatic Steatosis in Patients Undergoing Liver Resection: Comparison of US, CT, T1-weighted Dual-Echo MR Imaging, and Point-resolved 1H MR Spectroscopy, *Radiology*: Volume 256: Number 1-July 2010; Magnetic resonance imaging and spectroscopy accurately estimate the severity of steatosis provided the stage of fibrosis is considered. *Journal of Hepatology, Volume* 51, *Issue* 2, August 2009, Pages 389-397; both of which are incorporated by reference as if fully set forth herein), but spectroscopy remains the gold-standard.

Figure 3B:
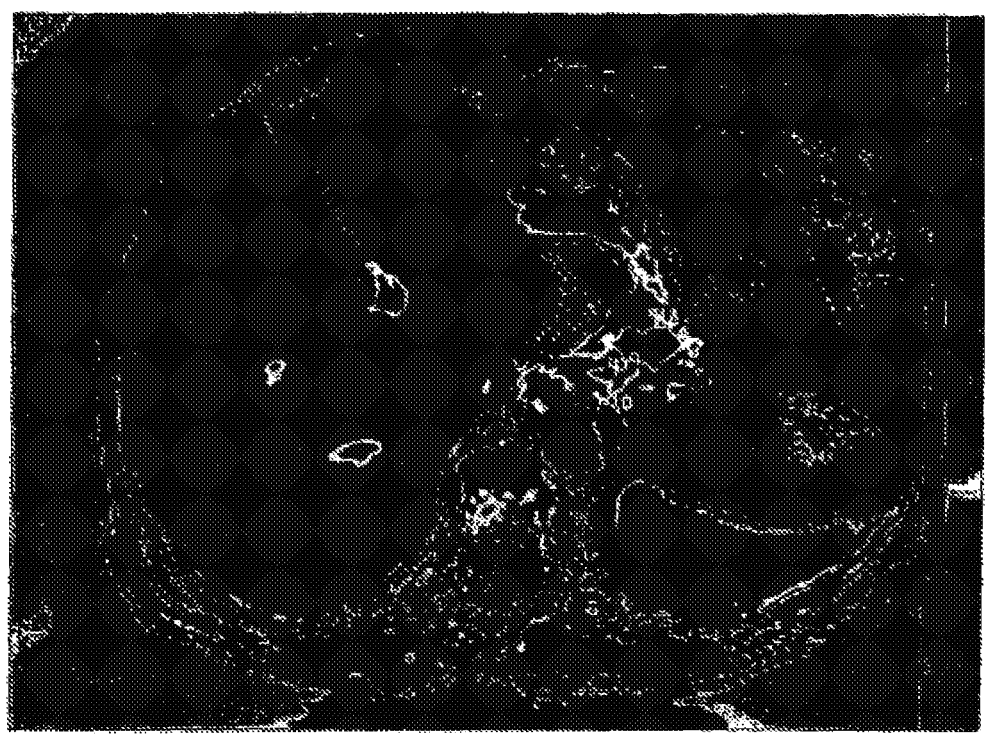
Figure 4:
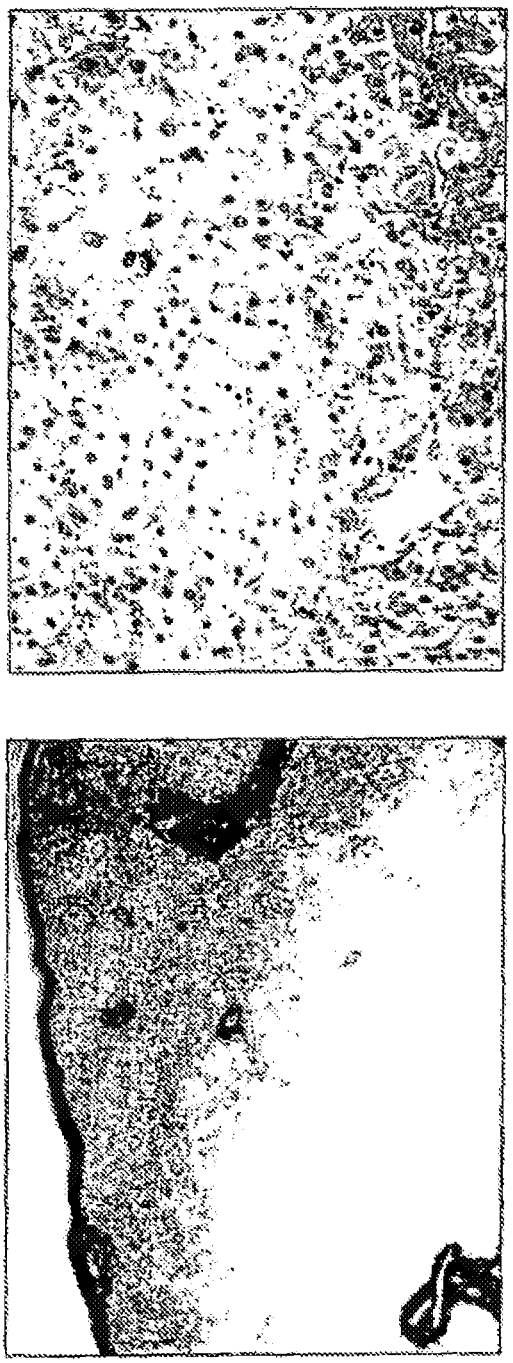
FIG. 4 shows a liver biopsy of the liver of FIG. 3B.

Shown in FIG. 3A, for example, is a transverse liver T1 map of a of a normal liver having a mean T1 value of 786 ms (+/−110 ms) and an MR spectroscopy value of less than 2%. FIG. 3B shows a transverse liver T1 map of a bariatric surgical patient (laparoscopic adjustable gastric band). T1 mapping showed a relatively low T1 relaxation time value of 765 ms. MR spectroscopy to measure liver fat presented a relatively modest value of 2.1%. Liver biopsy, see FIG. 4, indicated that this was an essentially normal liver having only mild steatosis.

Figure 5:
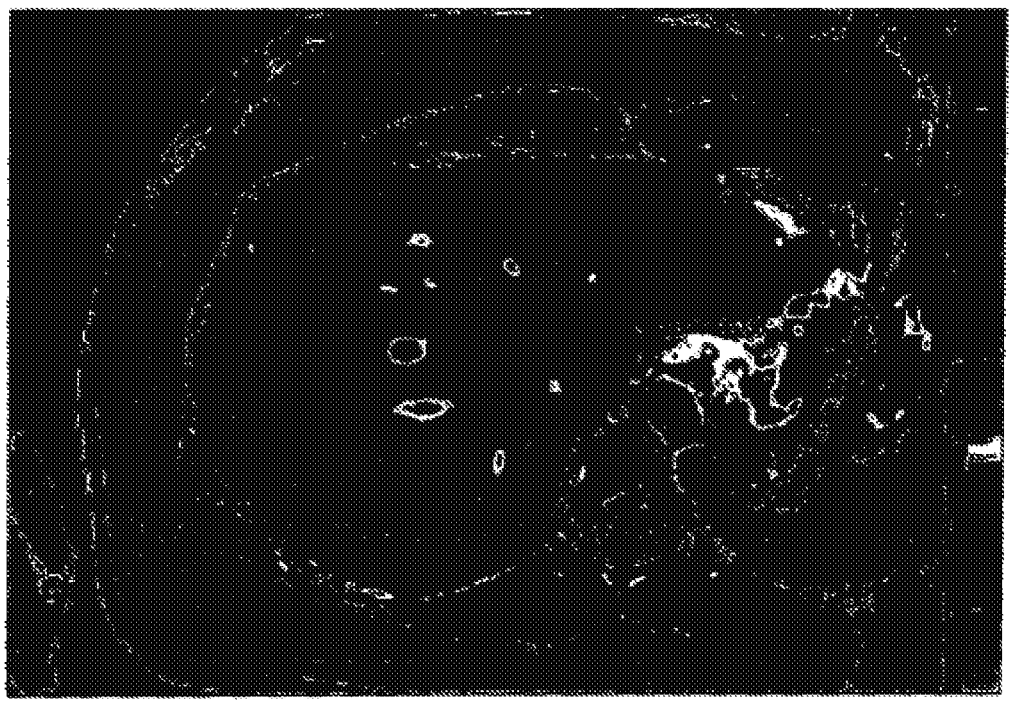
FIG. 5 is a transverse liver T1 map of a non-normal liver having elevated extracellular fluid and hepatic lipid content.

In contrast in a second bariatric surgical patient (laparoscopic adjustable gastric band) T1 mapping resulted in a relatively high value of 973 ms, while MR spectroscopy presented a value of 20.7% liver fat, see FIG. 5. Liver biopsy, shown in FIG. 6, confirmed the presence of non-alcoholic steatohepatitis (NASH).

We further discovered, however, that high hepatic iron can alter T1 values, lowering the values and causing an underreporting of extracellular fluid. In liver tissue with normal iron content, T1 mapping of the organ can reliably show differences in extracellular fluid content and thereby allow quantification of the degree of liver fibrosis. In liver tissue with excess iron content, T2* mapping can determine the degree of iron overload. Iron overload of the liver is toxic and causes fibrosis, and causes a reduced T2* value. The T1 value can be corrected in patients with reduced T2* to still enable assessment for fibrosis. Accurate quantification of HLC, in conjunction with assessment of iron and fibrosis, allows a multi-parametric approach enabling rapid non-invasive diagnosis of the type and/or severity of many common liver diseases, such as non-alcoholic fatty liver disease (NAFLD)/NASH, hepatitis, fibrosis in the absence of fatty liver (e.g., viral hepatitis) and iron overload, as well as others mentioned above.

Other methods can be used to measure iron content besides T2* mapping. Suitable methods also include T2 mapping (Guo H. et al., J Magn Reson Imaging, 2009 August; 30(2):394-400. Myocardial T2 Quantitation in Patients With Iron Overload at 3 Tesla; which is incorporated by reference as if fully set forth herein), and measuring one or more blood biomarkers, such as ferritin, transferrin, transferrin saturation, hepcidin, soluble transferrin receptor (sTfR) index (sTfR/log ferritin). MR spectroscopy can also be used to measure iron content and, thus, for iron overload. For example, the width of the $^1$H MRS spectra can indicate higher than normal iron loads.

Figure 7:
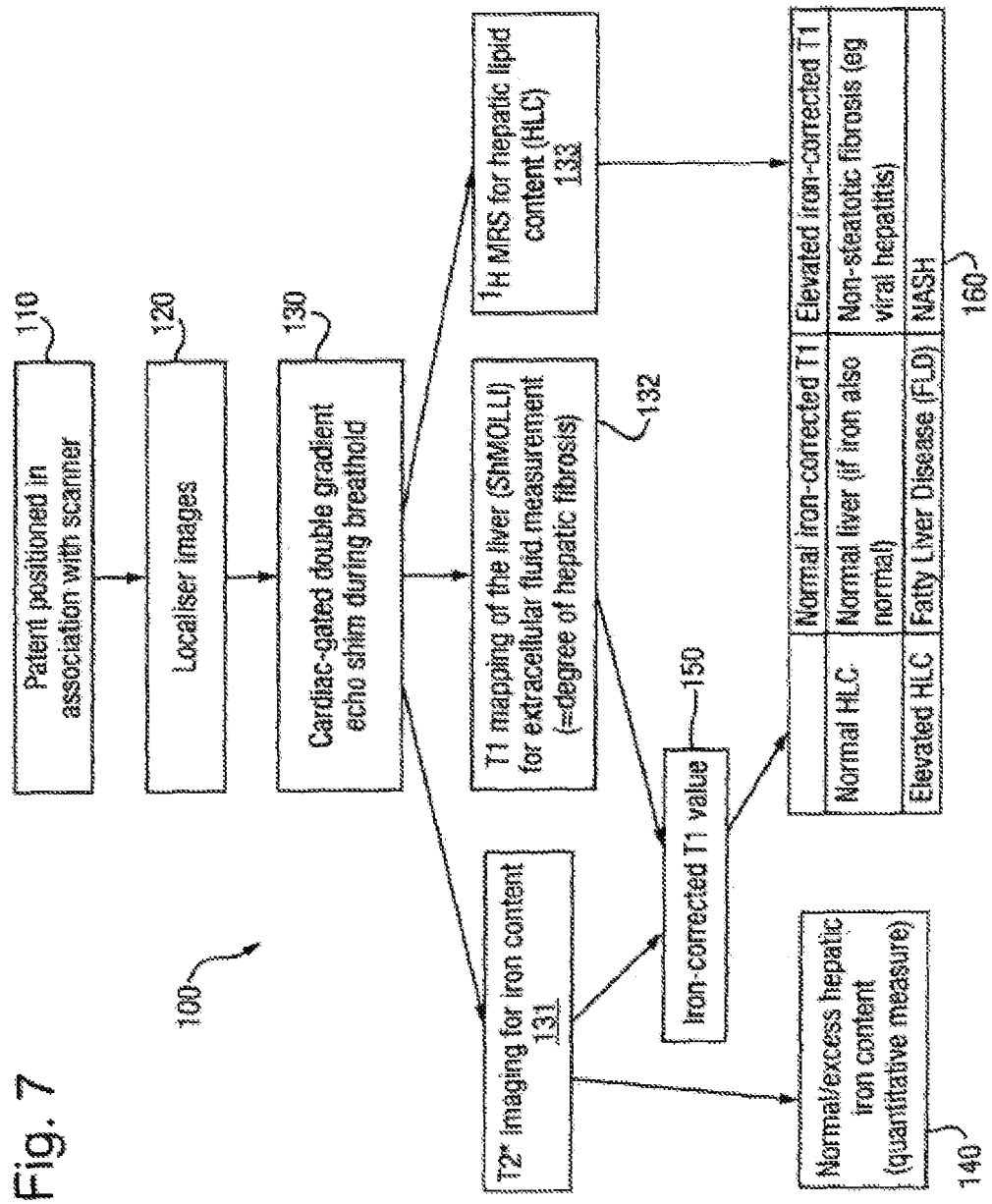
FIG. 7 depicts a flow chart for one embodiment for performing the multi-parametric magnetic (MR) diagnosis of a liver disclosed herein.

One embodiment of the present systems and methods for performing multi-parametric magnetic resonance (MR) diagnosis of a liver is illustrated in FIG. 7, which depicts a flowchart 100 for performing rapid imaging assessment of a liver.

A patient is first positioned 110 in association with a magnetic resonance (MR) scanner. Localizer images are performed 120, followed by cardiac-gated double gradient echo shim during breath-hold 130 using the scanner. T2* images can be taken for iron content measurement 131 along with mapping of spin-lattice T1 relaxation time of the liver for extracellular fluid (ECF) measurement 132 and MR spectroscopy for measurement 132 for hepatic lipid content (HLC).

The T2* images are used for quantitative measurement of hepatic iron content to determine whether normal or excess iron content is indicated. Where excess iron (iron overload) is found, the measured T1 values can be corrected 150 as described in more detail in the Methods and Examples below. A correction factor can then be applied to the measured T1 values 132 which in conjunction with the MR spectroscopy measurement for hepatic lipid content are then used for diagnosis 160 of the type and/or severity of common liver diseases, where excess iron is not found, it may not be necessary to apply a correction factor, in which case the measured T1 values can serve as a biomarker for liver disease without correction.

What may be considered "normal" iron content or "iron overload", or excess iron, can vary from patient to patient. One test for excess iron, however, is any condition where stainable iron is visible in a liver tissue biopsy, such as a positive result on a Perls' Stain. Another method is to measure dry weight iron from a separate liver biopsy—normal liver has less than 3 mmols per 100 g of liver tissue.

Diagnosis can be based on determining the presence or absence of iron overload. In one or more embodiments this may be done first. If iron overload is present, this is always pathological, and can be graded, for example by using the liver T2* value. The presence or absence of fatty infiltration of the liver can also be determined, quantified for example by spectroscopy. In one or more embodiments this may be done second. Further, the corrected T1 value for a given region of interest can determine the presence or absence of fibrosis, and its severity (FIG. 7). Characterising the parenchymal liver tissue by its iron, fat and fibrotic elements, as per the algorithm in FIG. 7, can lead to a diagnosis.

Quantitative mapping of spin-lattice (T1) relaxation time can use repeated inversion recovery (IR) experiments. The IR recovery experiments may include very short recovery periods that impact subsequent measurements depending on measured T1. One suitable approach for providing such experiments is the modified Look Locker inversion (MOLLI) recovery pulse sequence. MOLLI merges images from three consecutive inversion-recovery (IR) experiments into one data set, generating single slice T1 maps of the liver. It is generally described in Messroghli D R, Radjenovic A. Kozerke S, Higgins D M, Sivananthan M U, Ridgway J P. Modified Look-Locker inversion recovery (MOLLI) for high-resolution T1 mapping of the heart. Magn Reson Med 2004; 52:141-146 which is incorporated by reference as if fully set forth herein.

The MOLLI sequence, however, can require relatively long recovery epochs, thereby prolonging the measurement time and progressively increasing the estimation errors for the long T1 relaxation times or fast heart rates. The relatively long recovery epochs required for the MOLLI technique can require a relatively long breath-hold. The breath-hold is required in order for the patient to remain still during the scan to avoid movement of the liver. For some patients the breath-hold required for the MOLLI technique is too long. Some patients are not capable of holding their breath for the required time.

Another suitable approach for providing such experiments, particularly when a shorter breath-hold is desired is a shortened version of the MOLLI sequence (referred to as Sh-MOLLI) described herein which generates rapid and high-resolution spin-lattice (T1) maps without the use of contrast agents in a single short breath-hold involving less heartbeats and a shorter breath-hold than required for a MOLLI sequence. For some implementations, the shortened modified Look Locker inversion recovery (Sh-MOLLI) technique is performed in twelve heartbeats or less. Various embodiments of the Sh-MOLLI technique are based on an abbreviated T1 sampling scheme combined with the use of processing logic to distinguish between long and short T1 relaxation times in order to conditionally utilize available T1 samples for non-linear T1 fitting. See, generally, Piechnik S K, Ferreira V M, Dall'Armellina E, Cochlin L E, Greiser A, Neubauer S, Robson M D., Shortened Modified Look-Locker Inversion recovery (ShMOLLI) for clinical myocardial T1-mapping at 1.5 and 3 T within a 9 heartbeat breathhold, J Cardiovasc Magn Reson. 2010 Nov. 19; 12:69, which is incorporated by reference as if fully set forth herein.

One embodiment of the Sh-MOLLI technique is a method for performing T1 mapping requiring only a relatively short breath-hold. The method comprises performing consecutive inversion-recovery (IR) experiments that include front-loaded sampling followed by one or more subsequent experiments yielding a set of additional samples. The method further comprises conditionally including the subsequent one or more samples for the T1-mapping based on several concurrent estimates of T1 recovery time and respective fit errors associated with the subsequent samples.

In a further embodiment, T1 values that are larger than a predetermined interval (e.g., the heartbeat interval) are considered adequately estimated using just a single inversion recovery (IR) experiment. Additional IR experiments are used typically only to estimate short T1 values based on the respective estimates and the measures of additional improvement in the recovery curve. Thus, in an embodiment of the Sh-MOLLI technique, minimal recovery times are combined with conditional data reconstruction. In one embodiment, the conditional data reconstruction is conducted algorithmically based on certain conditions, equivalent to using binary weighting of input parameters. In another embodiment, the conditional data processing is achieved using weighted processing, for example using weights from a continuous scale.

Multiple datasets including a front-loaded data set are utilized based on original data to determine the inclusion of potentially suboptimal data samples. In accordance with such embodiments, progressive fitting of linear or non-linear models for these data sets are used to identify and reject samples identified as being suboptimal from available measurements. As described below, a first embodiment is directed to binary weighting of input parameters in model identification. While some embodiments incorporate binary weighting of input parameters in model identification, alternative embodiments incorporate weighting on a continuous scale whereby all samples are used.

In an embodiment of a Sh-MOLLI sequence, a first front-loaded group of samples with presumed optimal parameters is collected and fitted. Based on the results obtained from the first group of samples, additional samples and non-linear fitting may or may not be performed to improve accuracy over an extended range of parameters. Conditional data processing is performed and additional solutions are accepted when solutions fall within predetermined limits. Specifically, for some embodiments, additional solutions are accepted if the new solution is characterized by improved fit quality. Furthermore, a limit is placed on the processing time where further solutions are not sought when previous steps indicate that they are not necessary.

Reference is made to FIGS. 8A and 8B, which show a side-by-side simulated comparison of ECG-gated pulse sequence schemes for simulation of a) MOLLI and b) Sh-MOLLI at a heart rate of 60 bpm. Steady-state free precession (SSFP) readouts are simplified to a single 35° pulse each, presented at a constant delay time TD from each preceding R wave. The 180° inversion pulses are shifted depending on the IR number to achieve the desired shortest T1 (which may be but are not limited to such values as 100, 180 and 260 ms) in the consecutive inversion recovery (IR) experiments.

The plots shown in FIGS. 8A-B represent the evolution of longitudinal magnetization (Mz) for short T1 (400 ms, thin traces) and long T1 (2000 ms, thick lines). Note that long epochs free of signal acquisitions minimize the impact of incomplete Mz recoveries in MOLLI so that all acquired samples can be pooled together for T1 reconstruction. For Sh-MOLLI, the validity of additional signal samples from the 2nd and 3rd IR epochs is determined on-the-fly by progressive non-linear estimation so they can be used when deemed necessary or rejected when invalid.

Simulations were performed in IDL (Interactive Data Language ver. 6.1, ITT Visual Information Solutions) by implementing equations for the piece-wise calculation of longitudinal magnetization (Mz(t)) and the signal samples generated by a train of arbitrarily-spaced ideal excitation pulses. Inversion pulses were assumed to be perfect 180° excitations, and readout pulses were 35°. Both sequences had three IR epochs. Simulations were performed for MOLLI based on its optimized variant, which collects 3+3+5 samples in three consecutive IR epochs separated by long recovery periods (FIG. 8A).

As shown in FIG. 8B, with the Sh-MOLLI technique, 5+1+1 samples were collected in less than 10 heartbeats. It should be emphasized that the 5+1+1 sequence here is just one of various possible sequences that may utilized for Sh-MOLLI, and other sequence schemes may be implemented. IR epochs were separated by only one TRR (R-R interval). Abbreviated Sh-MOLLI recovery epochs mean that Mz can be severely affected by preceding IR epochs in the Sh-MOLLI sequence (FIG. 8B) so that the signal samples from the 2nd and 3rd IR obtained using Sh-MOLLI do not fit the IR equations as outlined for MOLLI. This problem is circumvented by conditional data analysis according to the algorithm described in more detail below.

For this example, given an adequate signal level, non-linear identification of T1 is always performed for samples 1-5 (S1-5) from the 1st IR, with samples from the 2nd (S6) and 3rd (S7) IR being used only if the estimated T1 values are short (<TRR) or very short (<0.4 TRR), respectively. Thus, in this embodiment, use of sample datasets S1-6) are accepted only if estimated T1 falls below a heartbeat interval (TRR), and use of sample datasets S1-7 are accepted only if estimated T1 falls below 0.4TRR. The final T1 is accepted only if the quality of fit sufficiently improves in comparison to the TRR. Simulations using both sequences outlined in FIGS. 8A-B were performed for T1 ranging from 50 to 2700 ms (50 ms increments) and for heart rate (HR) between 40-100 bpm (20 bpm increments) and adding noise representative of measurement conditions.

Having described the basic framework, details for implementing Sh-MOLLI are now described, which combines minimal recovery times with conditional data reconstruction. Embodiments of Sh-MOLLI may be implemented as 2, 3, or more inversion-recovery (IR) experiments split over a predetermined number of heartbeats to collect SSFP images with varying T1, typically on the order of 100-5000 ms, whereby the first IR experiment is "front-loaded" with more pulses. Conditional data processing is then performed to determine whether subsequent samples are to be included and with what impact they have on the final estimate.

Figure 9:
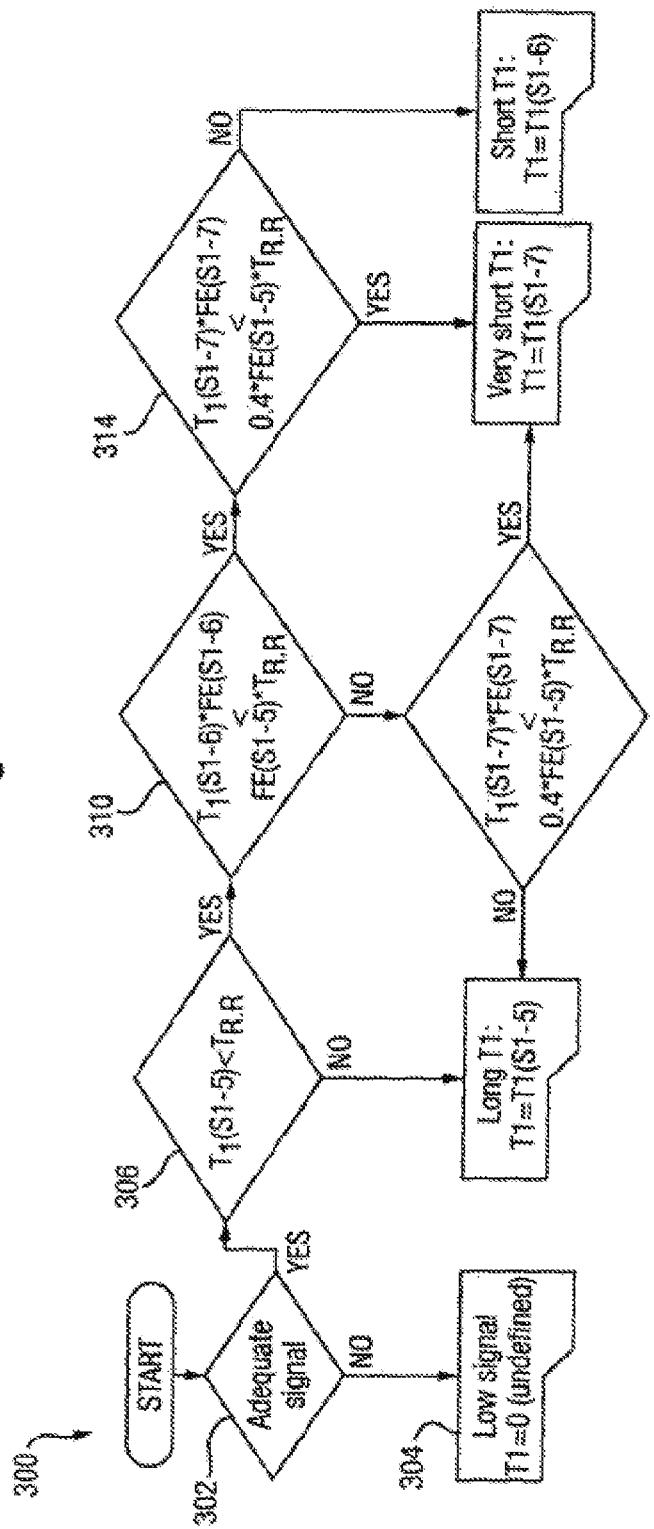
FIG. 9 is a flowchart for performing conditional data processing to establish appropriate processing sequence for example "long," "short," and "very short" T1 categories for T1 mapping of the liver.

Reference is made to FIG. 9, which is a flowchart 300 for performing an embodiment of the conditional data processing. An algorithm is implemented for the inclusion of samples to circumvent the impact of sub-optimally short recovery epochs in T1 estimation. The fit error (FE) is calculated as the square root of the sum of squared residuals divided by number of samples minus one. "S1-5" denotes the set of samples from the first inversion recovery. "S1-6" and "S1-7" denote the set of samples from the first inversion recovery supplemented by samples from consecutive IR experiments. $T_{R-R}$ is a heartbeat interval.

Note that while the first data set comprises 5 pulses followed by 1+1 pulses for this non-limiting example, the data sets are not limited to these numbers and other front-loaded schemes (e.g., 5+2+1, 5+1+2) may be implemented. In some embodiments, a front-loaded scheme can be implemented in which the number of samples from the first experiment exceeds the number of samples from a subsequent experiment. In other embodiments, a front-loaded scheme can be implemented in which the number of samples from the first experiment exceeds the number of samples from all subsequent experiments. Samples are obtained with potentially sub-optimally short recovery periods due to repeated Look-Locker Inversion recovery experiments (Piechnik S K, Ferreira V M, Dall'Armellina E, Cochlin L E, Greiser A, Neubauer S, Robson M D., Shortened Modified Look-Locker Inversion recovery (ShMOLLI) for clinical myocardial T1-mapping at 1.5 and 3 T within a 9 heartbeat breathhold, J Cardiovasc Magn Reson. 2010 Nov. 19; 12:69) contained within a single breath-hold. The fit error (FE) described above may also be replaced by another numerical representation of the empirical data consistency.

In accordance with one embodiment, conditional data processing is performed and Sh-MOLLI samples from the second and third IR are taken into account only if: 1) the estimated T1 is shorter than the R-R interval; and 2) if the second and third IR experiments improve non-linear fit. In the non-limiting example shown, a specific sampling method involving 5+1+1 samples in three IR experiments is used, separated by single recovery epochs.

In decision block 302, if an adequate signal is not present, then a low signal exists and processing stops (block 304). A predefined threshold may be used for this determination. An initial fit is performed using the first 5 samples, resulting in a T1 (S1-5) estimate—the recovery time for the first 5 samples. Processing continues based on whether the estimated T1 time is long (meaning equal to or longer than a heartbeat interval $T_{R-R}$) or short (meaning less than a heartbeat interval) (decision blocks 306, 310, 314).

For some embodiments, subsequent fits are performed to improve accuracy for the short T1 samples, only if T1 (S1-5) is less than the RR-period, the time between heartbeats (decision block 306). That is, if the T1 time for the first 5 samples is relatively short, subsequent samples are considered. Finally, the sample datasets of S1-6 and S1-7 are accepted and performed only if the estimated T1 falls below $T_{R-R}$ and $0.4*T_{R-R}$ respectively. Furthermore, the fit error (FE) normalized by the number of samples must be lower than the FE based on the first 5 samples (decision blocks 310, 314). Thus, a determination is made on how well subsequent samples (samples 6 and 7 in the non-limiting example of FIG. 9) match the recovery curve. This is done to ensure that noise and interference is not introduced by the latter samples following the front-loaded samples. Conditional reconstruction of incomplete recovery periods ensures that T1-mapping with a level of accuracy comparable to that by the MOLLI technique can be achieved in a shorter heartbeat breath-hold.

Figure 10:
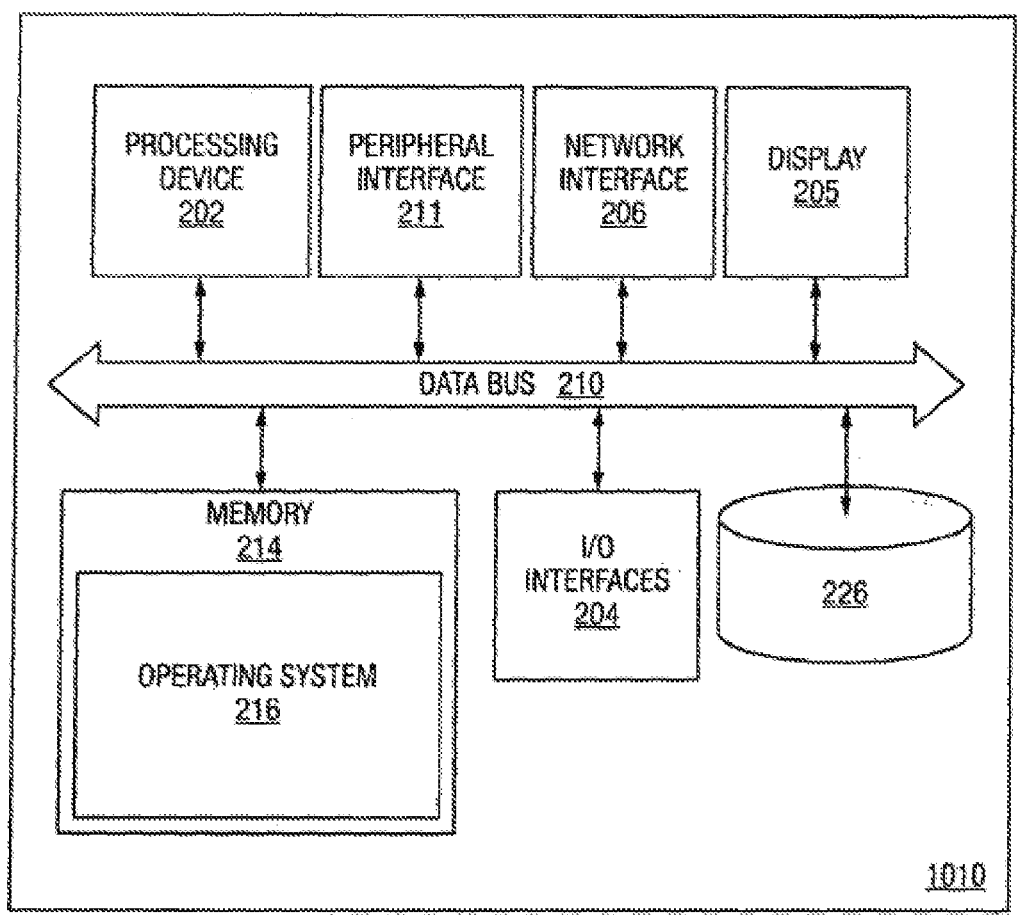
FIG. 10 is a schematic block diagram of an apparatus in which embodiments of the multi-parametric magnetic (MR) diagnosis of a liver disclosed herein may be implemented.

Reference is now made to FIG. 10, which depicts an apparatus 1010 in which the systems and methods for performing multi-parametric magnetic resonance diagnosis of a liver described herein may be implemented. The apparatus 1010 may be embodied in any one of a wide variety of wired and/or wireless computing devices, multiprocessor computing device, and so forth. As shown in FIG. 10, the apparatus 1010 comprises memory 214, a processing device 202, a number of input/output interfaces 204, a network interface 206, a display 205, a peripheral interface 211, and mass storage 226, wherein each of these devices are connected across a local data bus 210. The apparatus 1010 may be coupled to one or more peripheral measurement devices (not shown) connected to the apparatus 1010 via the peripheral interface 211.

The processing device 202 may include any custom made or commercially available processor, a central processing unit (CPU) or an auxiliary processor among several processors associated with the apparatus 1010, a semiconductor based microprocessor (in the form of a microchip), a macroprocessor, one or more application specific integrated circuits (ASICs), a plurality of suitably configured digital logic gates, and other well-known electrical configurations comprising discrete elements both individually and in various combinations to coordinate the overall operation of the computing system.

The memory 214 can include any one of a combination of volatile memory elements (e.g., random-access memory (RAM, such as DRAM, and SRAM, etc.)) and nonvolatile memory elements (e.g., ROM, hard drive, tape, CDROM, etc.). The memory 214 typically comprises a native operating system 216, one or more native applications, emulation systems, or emulated applications for any of a variety of operating systems and/or emulated hardware platforms, emulated operating systems, etc. For example, the applications may include application specific software which may be configured to perform some or all of the systems and methods for performing multi-parametric magnetic resonance diagnosis of liver disease described herein. In accordance with such embodiments, the application specific software is stored in memory 214 and executed by the processing device 202. One of ordinary skill in the art will appreciate that the memory 214 can, and typically will, comprise other components which have been omitted for purposes of brevity.

Input/output interfaces 204 provide any number of interfaces for the input and output of data. For example, where the apparatus 1010 comprises a personal computer, these components may interface with one or more user input devices 204. The display 205 may comprise a computer monitor, a plasma screen for a PC, a liquid crystal display (LCD) on a hand held device, or other display device.

In the context of this disclosure, a non-transitory computer-readable medium stores programs for use by or in connection with an instruction execution system, apparatus, or device. More specific examples of a computer-readable medium may include by way of example and without limitation: a portable computer diskette, a random access memory (RAM), a read-only memory (ROM), an erasable programmable read-only memory (EPROM, EEPROM, or Flash memory), and a portable compact disc read-only memory (CDROM) (optical).

With further reference to FIG. 10, network interface device 206 comprises various components used to transmit and/or receive data over a network environment. For example, the network interface 206 may include a device that can communicate with both inputs and outputs, for instance, a modulator/demodulator (e.g., a modem), wireless (e.g., radio frequency (RF)) transceiver, a telephonic interface, a bridge, a router, network card, etc.). The apparatus 1010 may communicate with one or more computing devices (not shown) via the network interface 206 over a network 118. The apparatus 1010 may further comprise mass storage 226. The peripheral 211 interface supports various interfaces including, but not limited to IEEE-1394 High Performance Serial Bus (Firewire), USB, a serial connection, and a parallel connection.

The apparatus 1010 shown in FIG. 10 may be embodied, for example, as a magnetic resonance apparatus, which includes a processing module or logic for performing conditional data processing, and may be implemented either off-line or directly in a magnetic resonance apparatus. For such embodiments, the apparatus 1010 may be implemented as a multi-channel, multi-coil system with advanced parallel image processing capabilities, and direct implementation makes it possible to generate immediate T1 maps available for viewing immediately after image acquisition, thereby allowing re-acquisition on-the-spot if necessary. Examples of apparatus in which the MOLLI and Sh-MOLLI sequences may be implemented are described in U.S. Pat. Nos. 5,993, 398 and 6,245,027 and U.S. Patent Application Publication No. 2011/0181285, which are incorporated by reference as if fully set forth herein.

The flowcharts of FIGS. 7 and 9 show examples of functionality that may be implemented in the apparatus 1010 of FIG. 10. If embodied in software, each block shown in FIGS. 7 and 9 may represent a module, segment, or portion of code that comprises program instructions to implement the specified logical function(s). The program instructions may be embodied in the form of source code that comprises machine code that comprises numerical instructions recognizable by a suitable execution system such as the processing device 202 (FIG. 10) in a computer system or other system. The machine code may be converted from the source code, etc. If embodied in hardware, each block may represent a circuit or a number of interconnected circuits to implement the specified logical function(s).

Although the flowcharts of FIGS. 7 and 9 show a specific order of execution, it is understood that the order of execution may differ from that which is depicted. For example, the order of execution of two or more blocks may be scrambled relative to the order shown. Also, two or more blocks shown in succession in FIGS. 7 and 9 may be executed concurrently or with partial concurrence. Further, in some embodiments, one or more of the blocks shown in FIGS. 7 and 9 may be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Also, any logic or application described herein that comprises software or code can be embodied in any non-transitory computer-readable medium for use by or in connection with an instruction execution system such as, for example, a processing device 202 in a computer system or other system. In this sense, each may comprise, for example, statements including instructions and declarations that can be fetched from the computer-readable medium and executed by the instruction execution system.

METHODS AND EXAMPLES

We conducted a study in which any adult patient referred for a diagnostic liver biopsy during a particular period of time was invited to take part. Exclusion criteria were any contraindication to 3 Tesla MR imaging (e.g., severe claustrophobia, pacemaker, metallic implant, pregnancy). Patients fasted for at least 6 hours on their study day before undertaking an MR scan. Venous blood was taken from subjects and sent for biochemical and haematological analysis.

For comparison, we scanned 100 normal adults with BMI 18.5-30 kg/m$^2$, excluding patients with pre-existing diabetes, cardiovascular conditions, hypercholesterolaemia, smoking habit and abnormal liver function enzymes. These patients did not have liver biopsies, but their imaging data was used to establish reference ranges for T1 (n=50, with paired measurements from lateral and medial liver segments) and hepatic lipid content (n=100).

MR Protocol

Patients were invited to attend for our multi-parametric 3 Tesla MR study prior to their liver biopsy.

Iron Content Imaging

A multi-gradient-echo acquisition with RF spoiling was used to calculate a T2* map of the liver. The field-of-view was optimised per patient, with a matrix size of 192×192, slice thickness of 3 mm, 2×GRAPPA acceleration and the same 200 ms delay after the R-wave before acquisition. The image was acquired in nine segments with a TR of 26.5 ms and flip angle of 20°. Echo times were selected as far as possible such that the signals from fat and water were in phase (TE=2.46, 7.38, 12.30, 17.22 and 22.14 ms). Fat-saturation and a double-inversion-recovery black blood preparation were used.

The iron content of the liver was shown to have marked effects on T1 and spectroscopy measurement, suggesting in particular interpretation of the T1 value with reference to the measured iron level.

Fat Measurement with $^1$H MRS

Hepatic lipid content (HLC) can be quantified using localised cardiac-triggered proton spectroscopy (Bredella M A, Ghomi R H, Thomas B J, Ouellette H A, Sahani D V, Miller K K, Torriani M., Breath-hold 1H-magnetic resonance spectroscopy for intrahepatic lipid quantification at 3 Tesla, J Comput Assist Tomogr. 2010 May-June; 34(3):372-6). At 3 Tesla, protons that are part of a methylene group (—CH2-) resonate at 1.3 ppm, while water resonates 4.7 ppm. We measured HLC as a percentage of the liver water content using $^1$H MRS in a 3 Tesla Siemens system (Tim Trio, Siemens Healthcare, Germany), using a stimulated echo (STEAM) sequence with water suppression. For this protocol, subjects lay supine in the scanner, and HLC was measured in the lateral right lobe of the liver, from where most percutaneous biopsy sampling occurs, and in the left lobe of the liver. Orthogonal axis hepatic localisers were obtained during end-expiratory breath-holds. Spectral acquisitions were all ECG-triggered to minimise motion artefact from vascular flow through the liver. A subject-dependent global calibration was used to minimise static magnetic field inhomogeneities. A spectroscopic voxel of interest (20×20×20 mm) was placed in a segment of liver carefully avoiding any blood or biliary vessels. A further calibration pulse sequence was used to determine the optimum water suppression pulse scaling factor to better characterise the lipid peak at 1.3 ppm. 5 acquisitions were obtained during end-expiration, with a repetition time (TR) of 2 seconds to allow for complete relaxation of the lipid signal between successive radiofrequency (RF) pulses. This required subjects to hold their breath and lie still for 12-14 seconds, which was comfortably managed by all of the participants. Spectroscopy parameters were set at an echo time (TE) of 10 ms, a mixing time of 7 ms, and 1024 points acquired at a bandwidth of 2000 Hz. We obtained spectra from 5 breath holds, 4 with water suppression on to collect lipid data, and one with water suppression off (3 spectra acquisitions, TR 4 secs for complete relaxation of the water peak between RF pulses) to determine the signal from hepatic water content. To reduce chemical shift displacement, scan frequency was set at 1.3 ppm during water-suppressed acquisition, and at 4.7 ppm during the water-unsuppressed acquisition.

Figure 14:
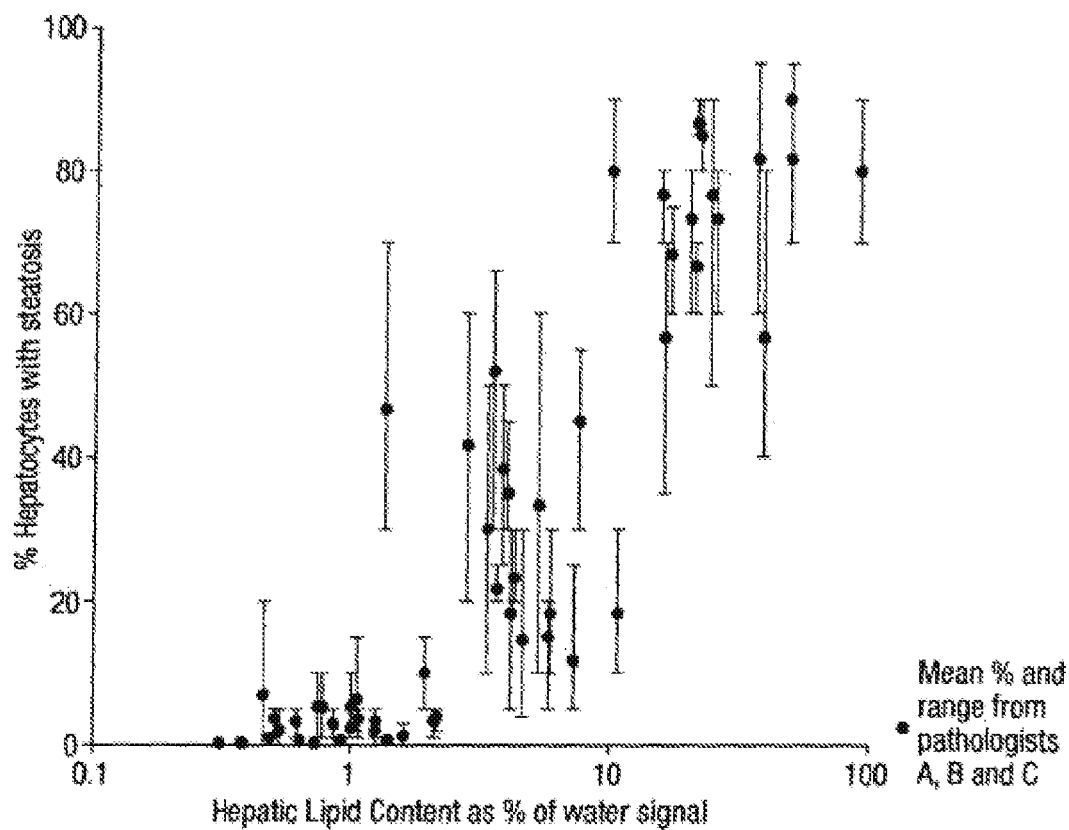
FIG. 14 shows HLC measured by MR spectroscopy and liver biopsy.

With reference to FIG. 14, results from MR assessment of liver fat content were compared to blinded analysis by three pathologists. For the percentage of hepatocytes with visible lipid inclusions, shown below, there was considerable variance in assessment between pathologists, especially for values of hepatic lipid content between 2 and 12%. The trivariate weighted kappa statistic from pathologists A, B and C was 0.75. Spectroscopy predicted the mean % steatosis from the three pathologists very well ($r_s$=0.88, p<0.001). Correlation with individual pathologists was also good: Path A $r_s$=0.83, Path B $r_s$=0.86, Path C $r_s$=0.85, all p<0.001.

Fibrosis Imaging with T1 Mapping

A T1 relaxation time map was acquired using the aforementioned Sh-MOLLI sequence, in particular, a 5+1+1 sequence, (Piechnik S K, Ferreira V M, Dall'Armellina E, Cochlin L E, Greiser A, Neubauer S, Robson M D., Shortened Modified Look-Locker Inversion recovery (ShMOLLI)

for clinical myocardial T1-mapping at 1.5 and 3 T within a 9 heartbeat breathhold, J Cardiovasc Magn Reson. 2010 Nov. 19; 12:69) in a transverse plane through the spectroscopic voxel of interest in the lateral right lobe of the liver. A subject—dependent frequency adjustment was carried out during end-expiration. The Sh-MOLLI sequence uses samples the T1 recovery curve using single-shot steady state free precession (SSFP) acquisitions using the following parameters:

TR 2.14 ms, TE 1.07 ms, flip angle of 35°, field-of-view was optimised per patient, Matrix 192×144, with GRAPPA acceleration of 2 with 24 reference lines, yielding a typical interpolated voxel size 0.9×0.9×6 mm. Images were acquired 200 ms after the ECG R-wave and the total time for each SSFP acquisition was 206 ms. Normal ranges for T1 were determined with measurements taken from the left and right hepatic lobe from transverse Sh-MOLLI images from 50 normal volunteers. This demonstrated that the Sh-MOLLI recovery technique provided suitable T1 mapping of the liver.

Image Analysis

MRS Data was analysed offline by a researcher blinded to the anthropometric measurements and imaging data using AMARES in the jMRUI package and home written software running within MATLAB 2010b. Signals from different coil elements in each breath-hold and were combined using a customised programme in MATLAB.

Individual spectra were phase and frequency corrected prior to summation. HLC was expressed as Amplitude of the CH2 peak/Amplitude of the water peak×100%

T1 & T2*Analysis was performed on the console by an MR physicist blinded to the patient data. T1 values were only accepted if $R^2$ of the inversion recovery curve fit exceeded 99%. Regions of interest (ROIs) in the T1 maps were manually contoured to correspond with the spectroscopic voxels in the lateral right lobe of the liver and in the left lobe of the liver, excluding blood and biliary vessels. The mean T1 relaxation times in these ROIs were recorded.

T2* maps were accepted based on visual inspection of the source images, excluding images with artefacts due to blood or biliary vessels, respiration or other motion, and avoiding air-tissue interfaces when placing the ROIs. The mean T2* value was recorded for each ROI.

An MR fibrosis score algorithm was used to score the degree of fibrosis, based on the measured T1 and T2* values. If hepatic iron content was normal, then MR fibrosis can be graded. An example of such grading is presented in Table 1 below:

TABLE 1

| T1 value | MR fibrosis score with normal liver iron |
|---|---|
| <800 ms | 0 |
| 800-850 | 1 |
| 850-900 | 2 |
| 900-950 | 3 |
| 950-1000 | 4 |
| 1000-1050 | 5 |
| >1050 | 6 |

If liver iron was elevated, a correction factor was applied, in particular the MR fibrosis score was increased. As one example, with a T2*13-15 ms, then the score was increased by +1; moderate iron overload (T2*11-13 ms) added +2, severe iron loading (T2*7-11 ms) added +3, and toxic iron overloading (T2*<7 ms) added +6.

Alternative ways of interpreting the T1 value in the context of a patient's iron load are possible. These include for example:

1. A correction factor based on blood biomarkers, such as ferritin, transferrin, transferrin saturation, hepcidin, soluble transferrin receptor (sTfR) index (sTfR/log ferritin).
2. A correction factor based on patient history of transfusion, age, disease and genotype.
3. Directly correcting the measured T1 value using an empirical relation such as T1 corrected=T1 measured+ 420−(20×T2* measured)
4. Using the width of the 1H MRS spectra to determine the effect of iron on the T1 signal—for example normal liver with normal iron load yield narrow spectral peaks, whereas higher iron loads have broader spectral peaks Histopathology An experienced hepatobiliary histopathologist evaluated the liver biopsy samples from all patients, blinded to the MR results. All samples were graded for steatosis, fibrosis and iron content. Hepatic fat content was measured by determining the percentage of macrovesicular and microvesicular steatosis and graded as 0 (0-5%), 1 (5-33%), 2 (34-65%) and 3 (>66%). As above, interobserver variation in the assessment of hepatic steatosis was assessed by asking three expert liver pathologists to analyse the patients' slides blinded to each other and to the clinical data (FIG. 14).

Fibrosis was graded as per the ISHAK scoring system. Ishak K., et al., Histological grading and staging of chronic hepatitis. J Hepatol. 1995; 22: 696-699, which is incorporated by reference as if fully set forth herein. Generally, liver fibrosis can be described as the excessive accumulation of extracellular matrix proteins including collagen that occurs in most types of liver diseases. Chronic liver diseases lead to fibrosis which leads to derangement of the architecture, portal hypertension and may produce such an irreversible rearrangement of the circulation as to cause cirrhosis. Cirrhosis is a consequence of chronic liver disease characterized by replacement of liver issue by fibrosis, scar tissue and regenerative nodules (lumps) that occur as a result of a process in which damaged issue is regenerated. The differences between morphological appearance, description, stage scoring and liver fibrosis measurement are reported by Standish R. et al (An appraisal of the histopathological assessment of liver fibrosis. Standish R A, Cholongitas E, Dhillon A, Burroughs A K, Dhillon A P Gut. 2006 April; 55(4):569-78, which is incorporated by reference as if fully set forth herein) presented in the following FIG. 21 therefrom.

Stainable iron was estimated using a Perl's histochemical stain and semi-quantified using a four tier grading system.

Results

Figure 11A:
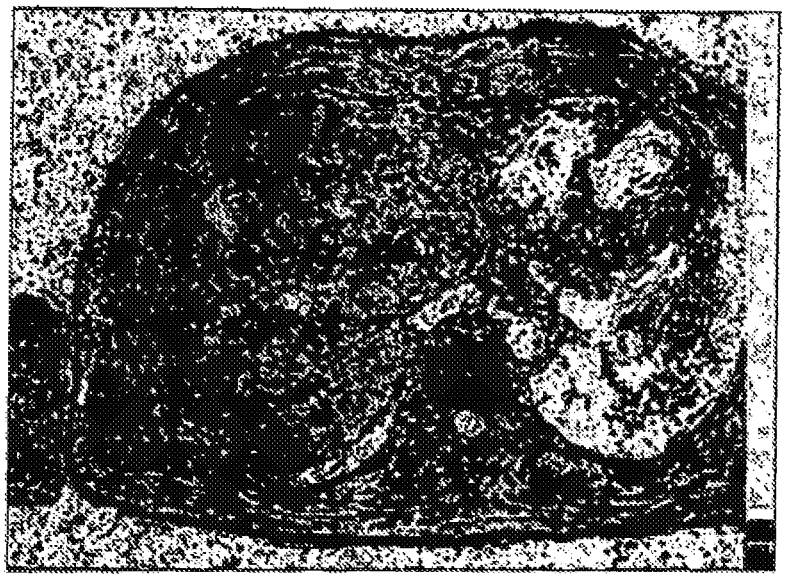
FIGS. 11A and 11B are representations of slice maps of a liver for iron assessment with T2* measured in lateral liver showing a patient with normal iron level (FIG. 11A) and a patient with mild iron overload (FIG. 11B).
Figure 11B:
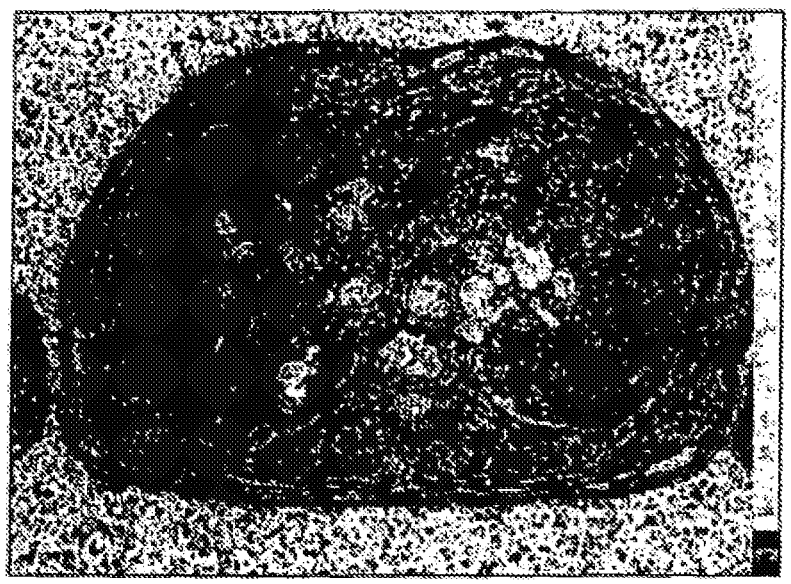

The study included T1 values from 50 normal adults, and biopsy and imaging data from 69 patients, mean age 52±standard error 2, of whom 21 were female. 45 patients had normal liver iron content, measured by T2* mapping (T2* range 15-30 ms), and 24 patients had evidence of elevated iron content consistent with T2*<15 ms. For example, in FIG. 11, slice maps of liver iron assessment with T2 measured in lateral liver are shown. The patient on the left (FIG. 11A) is normal (21.3 ms), which the one on the right (FIG. 11B) was mild iron overload (13.5 ms).

Figure 13:
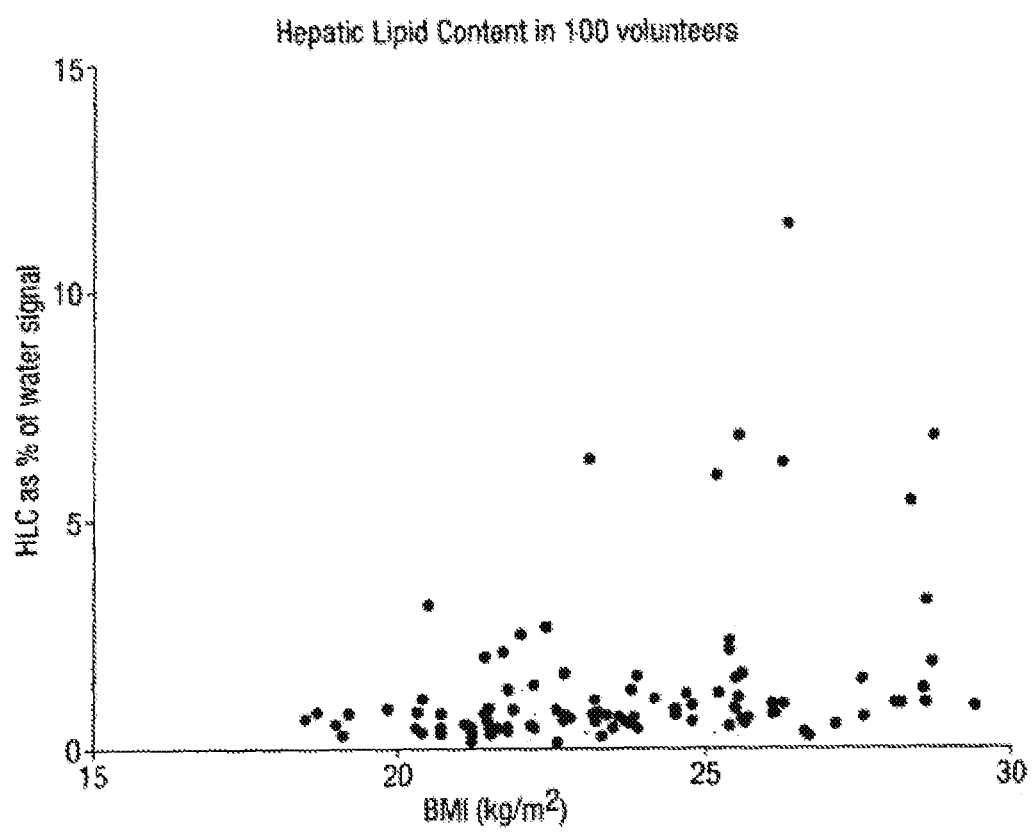
FIG. 13 shows HLC measured in 100 normal volunteers.

Ranges for T1 for the 50 normal volunteers (i.e., the "normal ranges") were determined as 786±110 ms (mean±2SD, see FIG. 12). Hepatic lipid content (HLC) was measured in 100 normal volunteers, determined as having a body mass index (BMI) in the range of 18-30 kg/m². Normal HLC was determined as 1.3±3.4%, with a median of 0.75% and an interquartile range of 0.47-1.25% (0-4.7%; see FIG. 13).

HLC measured by MR spectroscopy (MRS) correlated well with histological assessment (liver biopsy) for hepatic steatosis, with $r_s$=0.88, p<0.001 (FIG. 14).

Figure 15:
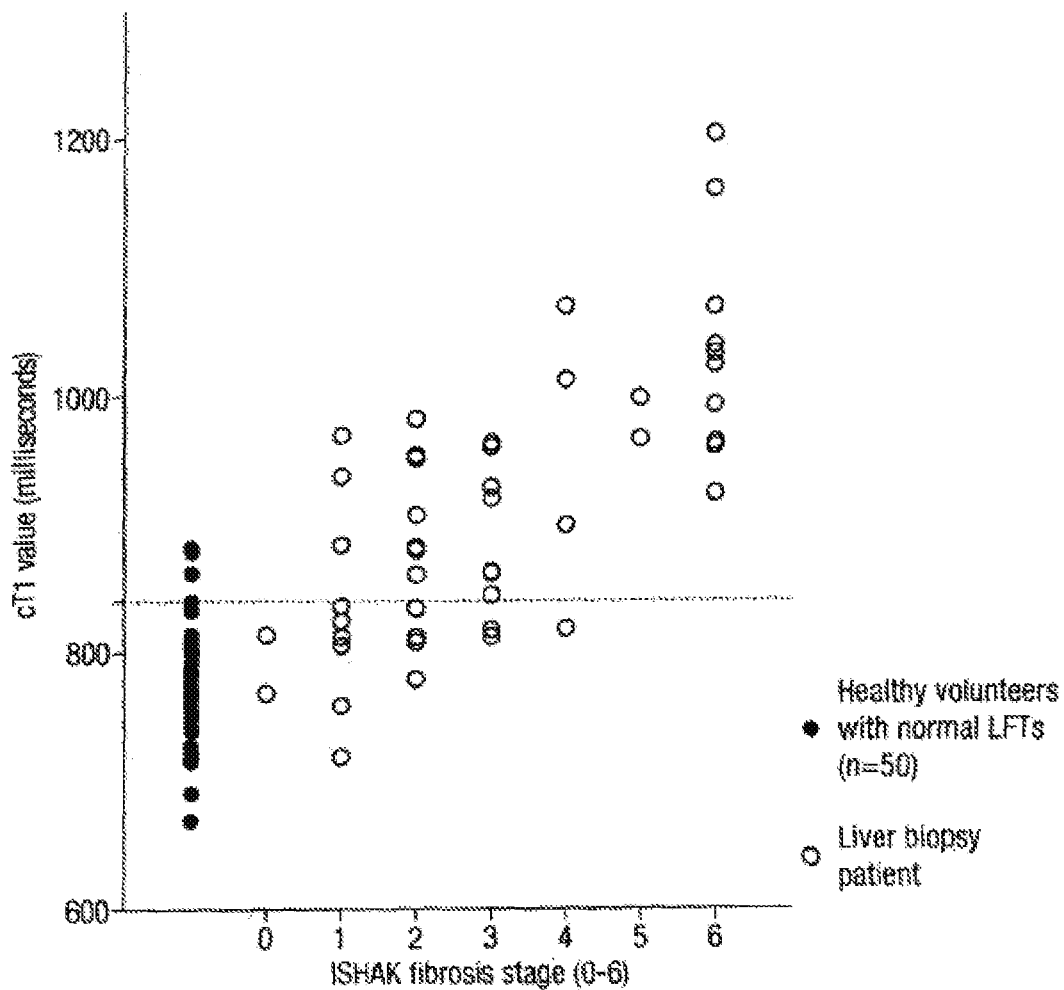
FIG. 15 shows liver T1 values correlated with ISHAK score for hepatic fibrosis.

For the 45 patients without MR evidence of iron overload, liver fibrosis was detectable with T1 mapping. Not only was there a clear correlation between T1 and ISHAK score ($r_s$=0.89 and p<0.001, FIG. 15), but every normal iron patient with significant fibrosis had T1>900 ms. Iron corrected T1 (cT1) predicted the degree of fibrosis in patients, regardless of the aetiology of disease. Referring to FIG. 15, there was a close correlation between the cT1 value for a region of interest and the Ishak fibrosis stage ($r_s$=0.71, p<0.001). cT1 values from 50 volunteers with presumed healthy livers (blue) and from 50 liver biopsy patients (red) were acquired with no knowledge of any clinical data or the indication for biopsy. The Ishak fibrosis score shown is the consensus score from 3 histopathologists with knowledge of the clinical data. The dotted line at cT1=840 ms has a sensitivity of about 90% and a specificity of about 88% for the detection of Ishak>2.

Figure 16:
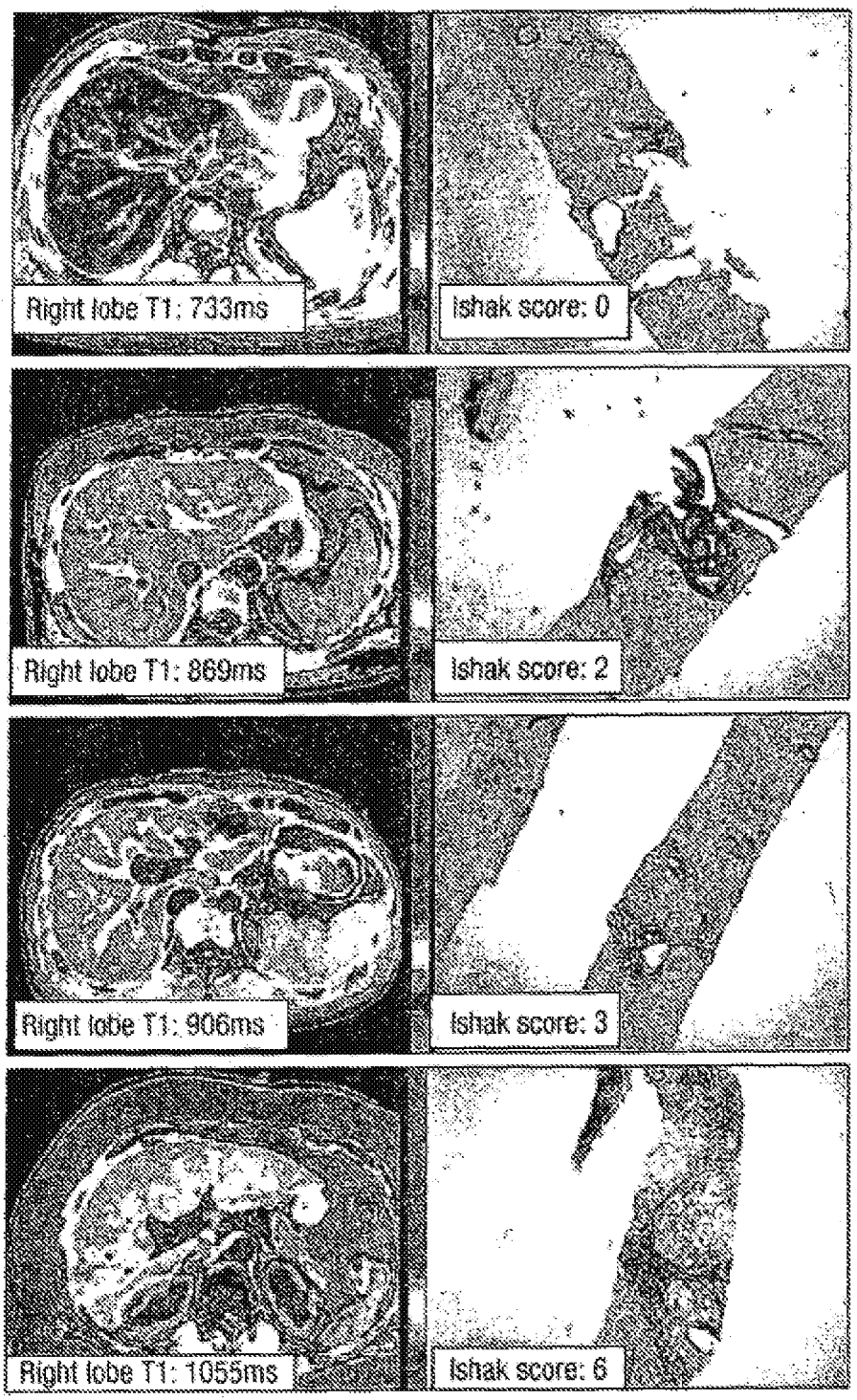
FIG. 16 shows examples of data acquired for fat and fibrosis imaging in normal iron content patients.
Figure 17:
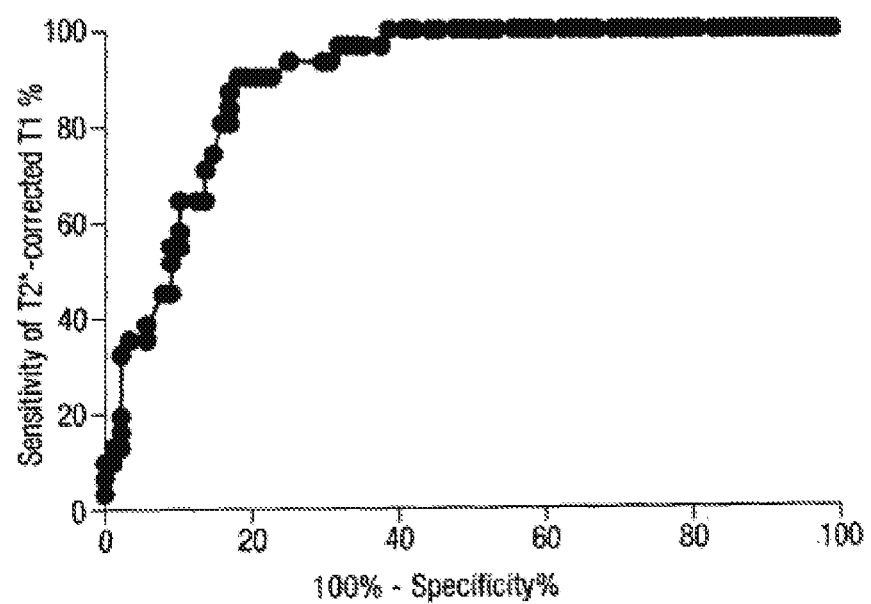
FIG. 17 depicts an ROC curve for the assessment of liver fibrosis by an embodiment of the present system.

As a combined MR protocol, every patient with normal hepatic iron content and significant fibrosis was correctly identified. FIG. 16 depicts viral hepatitis fibrosis staging. Shown are examples of transverse liver cT1 maps taken at the level of the spleen from 4 patients with corresponding Sirius Red stained liver biopsies for fibrosis (Ishak 0-6). In the fifty liver biopsy patients studied, 19 had viral hepatitis. The appearance of the maps, and the quantitative measure of ECF, clearly correlated with the degree of fibrosis as assessed by the Ishak score ($r_s$=0.88; p<0.001), FIG. 17 depicts an ROC curve for the assessment of liver fibrosis by our present multi-parametric system using MR imaging. This ROC curve uses the normal volunteers (n=50) with presumed normal livers, the patients with ISHAK 0-2 (n=38) with mild liver fibrosis as the control group, and patients with ISHAK>2 as the disease group (i.e., moderate to severe liver fibrosis). The Fe-corrected T1 values accurately predict the presence of significant fibrosis, with an area under ROC of 0.89.

Further, our method of liver assessment allows non-invasive, safe measurement of changes in liver tissue. We have shown that certain interventions can cause improvement in liver function in different diseases, and this can be quantified.

Example 1. Weight Loss Causes Regression of Fat and Fibrosis

Figures 18A, 18B:
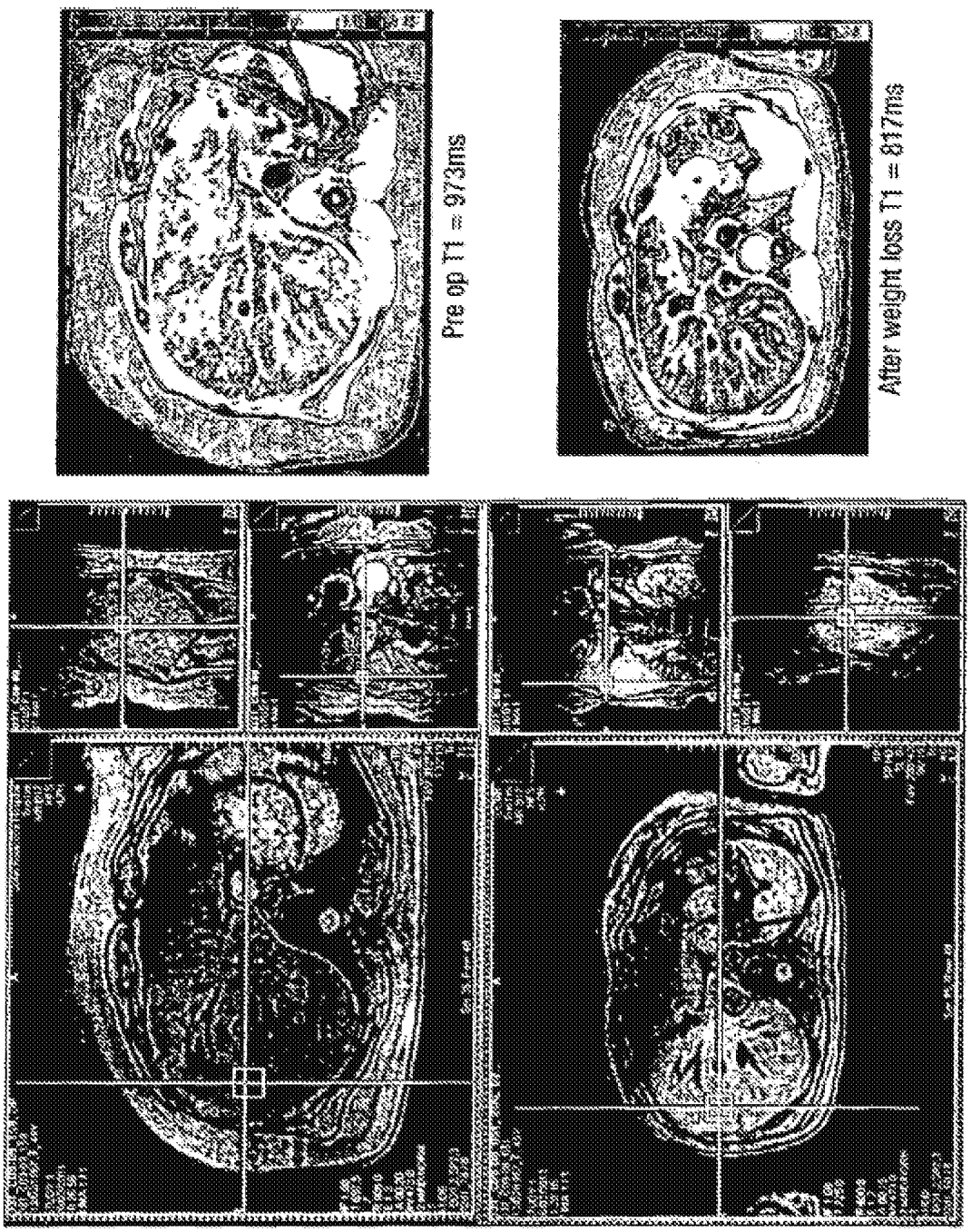
FIGS. 18 (A-B) show an improvement in steatohepatitis can be measured non-invasively using an embodiment of the present system.
Figure 19A:
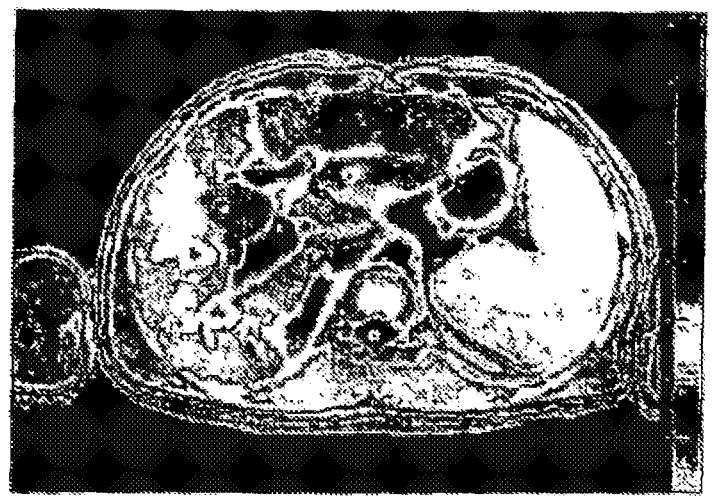
FIGS. 19 (A-D) show an improvement in hepatic inflammation in response to immunosuppressive drug therapy can be measured by an embodiment of the present system and method.
Figure 19B:
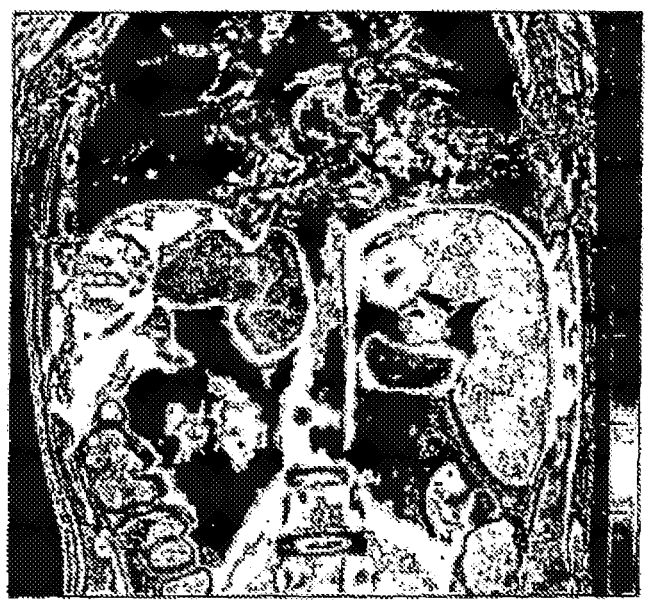
Figure 19C:
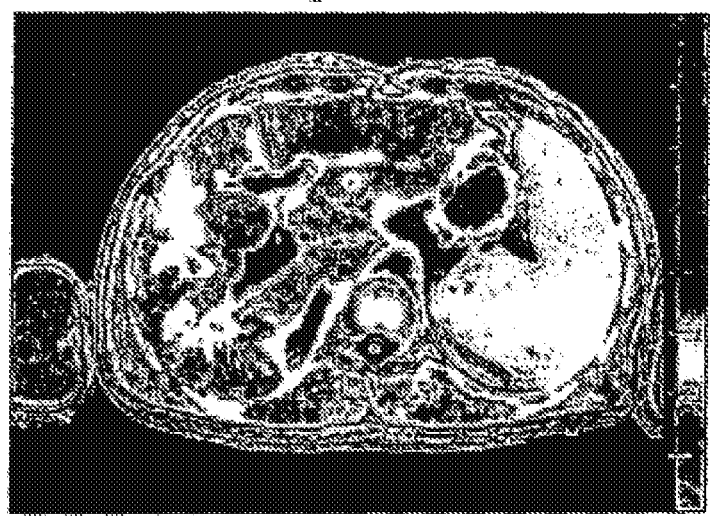
Figure 19D:

FIGS. 18 A-B show an improvement in steatohepatitis can be measured non-invasively using our present system and method. A 44 year old women had liver assessment with multi-parametric MR before and one year after gastric bypass surgery. Preoperative BMI 34.3 kg/m² (top), and 1 year Postoperative BMI 24.4 kg/m² (lower) images are shown. Preoperative MR showed 20% liver fat and a corrected T1 of 973 milliseconds, suggesting moderate-severe hepatitis. Histology of liver biopsy taken at time of operation showed 90% of hepatocytes had lipid inclusions, and an ISHAK score of 3, with marked pericellular fibrosis as well. This confirmed the MR findings. One year later, her liver fat content had reduced from 20% to 2%, and her corrected liver T1 had also fallen from 973 to 817 milliseconds. These images depict how the multi-parametric MR assessment of our present disclosure show improvement in NASH with treatment, without the need for liver biopsy.

Example 2. Steroids and Azathioprine Cause Improvement in Liver Inflammation in Autoimmune Liver Disease FIGS. 19 A-D show an improvement in hepatic inflammation in response to immunosuppressive drug therapy can be measured with our multi-parametric system and method. These figures show the effect of steroids and azathioprine on autoimmune liver disease. This patient was diagnosed with complex liver disease, likely primary sclerosing cholangitis. He was treated with immunosuppression. Repeat MR assessment one year later suggests marked improvement in his liver fibrosis. Initial scan (FIGS. 19 A and B). Coronal (B) and transverse (A) images clearly show regional differences in T1, and therefore ECF. He had a percutaneous liver Bx—showing severe inflammation and 6/6 fibrosis. Also of note, enlarged spleen and portal vasculature was indicated. Seven months later (FIGS. 19 C and D), marked improvement in the swelling of his liver, and many segments appear unaffected. The spleen is also less swollen/engorged.

Figure 20:
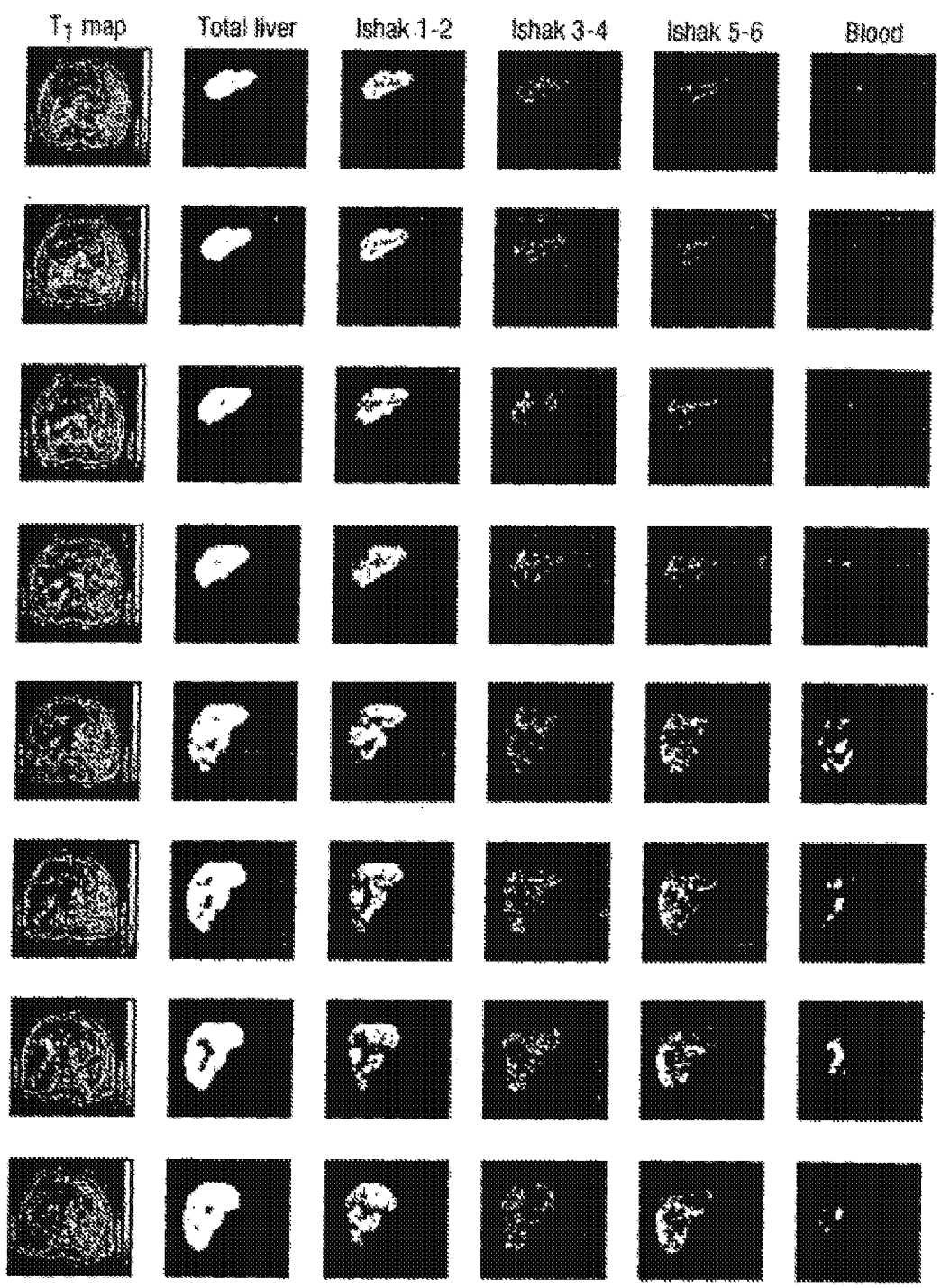
FIG. 20 depicts an example of quantitation of the volume of liver damage using an embodiment the present system and method.

Lastly, our system and method of liver assessment can further allow for quantitation of the volume of liver damage, when present. FIGS. 18A-B and 19A-D represent 2-D T1 maps or image slices. We can similarly obtain a stack of slices, or T1 maps, and make a 3-D reconstruction of the liver or a region of interest (ROI) within the liver. By doing so, we can determine a volume percent of injured tissue verses normal tissue within the region of interest (ROI) or the liver as a whole. For example, we can determine which T1 values correspond to different levels of disease over a large region of interest. Mean values can be used to derive ranges of T1 values that define an Ishak score for each individual voxel (for example, a 1 mm×1 mm×8 mm value) comprising the region of the outline. By acquiring a data set that encompasses a large ROI or even the whole liver, by for example a series of 2-D image slices, or a true 3-D acquisition, we can generate an Ishak map of the region of interest or even the entire organ. The image slices or segmentations can be visualized, as for example in FIG. 20, and can be used to evaluate the degree of damage in the liver. In FIG. 20 threshold values were determined for the voxel-wise T1 maps that allow segmentation of the liver into areas with different degrees of injuries. In this particular example, the outline of liver was manually traced (though it need not be). The segmentation into different levels of damage, however, was dated driven using the thresholding approach. In the present example, blood was also segmented out. An example of this approach is shown in Table 2 below in which the total volume of the liver is broken down into different Ishak scores indicating different degrees of injury for different volumes of the liver. For each Ishak score, a volume of the liver is approximated using the above approach providing an approximation of different levels of disease over the total liver.

TABLE 3

| | Volume |
|---|---|
| Total liver | 1120.2799 ml |
| Ishak 1 | 305.6532 ml |
| Ishak 2 | 62.6519 ml |
| Ishak 3 | 87.7387 ml |

TABLE 3-continued

| | Volume |
|---|---|
| Ishak 4 | 69.3034 ml |
| Ishak 5 or 6 | 246.2022 ml |

CONCLUSIONS

The results of our study demonstrate that the spectrum of liver disease that can be studied is broad and encompasses several phenotypes with potentially important MR features that allow better tissue characterisation. This data shows that tissue characterisation with MR allows the diagnosis of the type and severity of many common types of liver disease as well as liver biopsy. Multi-parametric liver tissue characterisation, however, is quicker (<20 minutes) and safer (non-invasive, no contrast required). It is also much cheaper than current care, which requires a 6 hour stay in hospital following biopsy with respective nursing, physician and pathologist time. In some liver conditions, it is hoped that this technique will replace liver biopsy (e.g., assessment of chronic hepatitis C and monitoring of fatty liver disease progression). In instances when it will not prove diagnostic, it will certainly complement histological data in determining additional potentially useful disease aetiology (e.g., iron overload conditions). The ISHAK algorithm is the most accepted scoring system for chronic hepatitis, although it has not been validated for use in many other conditions, including NASH, Wilson's disease, al antitrypsin deficiency, or chronic alcohol abuse, many of which are highly prevalent.

In discussion with hepatologists, it was agreed that if the techniques of the present systems and methods for performing multi-parametric magnetic resonance diagnosis of the liver were validated, then the 5 patients with T1<900 ms would not have been referred for biopsy as the only clinical question was whether they had significant fibrosis.

It should be emphasized that the above-described embodiments are merely examples of possible implementations. Other methods for providing inversion recovery (IR) experiments may be used. Further, similar protocols can be performed at different MR field strengths, for example, at 1.5 Tesla. Many variations and modifications may be made to the above-described embodiments without departing from the principles of the present disclosure. All such modifications and variations are intended to be included herein within the scope of this disclosure and protected by the following claims.

The invention claimed is:

1. A computer-implemented method for determining the presence or absence of liver disease in a subject, the method comprising the steps:
   a) positioning a subject in association with a magnetic resonance (MR) scanner;
   b) obtaining a measured value of the subject's liver for extracellular fluid using the magnetic resonance (MR) scanner, wherein the measured value of the subject's liver for extracellular fluid is obtained by using T1 mapping;
   c) from a measurement for the iron content of the subject's liver which has been obtained from the subject's liver determining whether iron overload is indicated;
   (d) if iron overload is indicated, correcting the measured value for extracellular fluid in the subject's liver; and
   (e) determining from:
      (i) the measurement for the iron content of the subject's liver,
      (ii) the corrected measurement for the extracellular fluid in the subject's liver, and
      (iii) a measurement for the hepatic lipid content (HLC) of the subject's liver which has been obtained from the subject's liver, wherein the measurement of the subject's liver for hepatic lipid content (HLC) is obtained by using one or more of MR spectroscopy, Dixon in and out of phase imaging, or dual-echo techniques,
   a presence or absence of liver disease in the subject.

2. The method of claim 1, wherein the measured value of the subject's liver for extracellular fluid is obtained by using T1 mapping, the measurement of the subject's liver for iron content is obtained by using T2* imaging and the measurement of the subject's liver for hepatic lipid content is obtained by using MR spectroscopy.

3. The method of claim 2, wherein the measurement of the subject's liver for hepatic lipid content is obtained by using $^1$H MR spectroscopy.

4. The method of claim 2, wherein the T1 mapping is performed using a modified Look Locker inversion (MOLLI) recovery pulse sequence or a shortened modified Look Locker inversion recovery (Sh-MOLLI) sequence.

5. The method of claim 1, wherein the measurement of the subject's liver for iron content is obtained by using one or more of T2 mapping, T2* mapping, measuring one or more blood biomarkers, or MR spectroscopy.

6. The method of claim 1, wherein the liver disease consists of one or more of non-alcoholic fatty liver disease (NAFLD), non-alcoholic steatohepatitis (NASH), high hepatic lipid content, hepatic fibrosis, autoimmune hepatitis, primary biliary cirrhosis, primary sclerosing cholangitis, viral hepatitis, chronic hepatitis, drug-induced hepatitis, haemochromatosis, thalassaemia, alcoholic hepatitis, alcoholic liver cirrhosis, portal hypertension, vascular liver disease, idiopathic hepatic fibrosis, sarcoidosis, hepatic cysts, or hemangiomas.

7. A system, comprising:
   a magnetic resonance (MR) scanner;
   at least one computing device;
   at least one application executable in the at least one computing device, the at least one application comprising logic that:
   a) obtains a measured value of a subject's liver for extracellular fluid using the magnetic resonance (MR) scanner, wherein the measured value of the subject's liver for extracellular fluid is obtained by using T1 mapping;
   b) from a measurement for the iron content of the subject's liver which has been obtained from the subject's liver, determines whether iron overload is indicated;
   c) if iron overload is indicated, corrects the measured value for extracellular fluid in the subject's liver; and
   d) determines from:
      (i) the measurement for the iron content of the subject's liver,
      (ii) the corrected measurement for the extracellular fluid in the subject's liver, and
      (iii) a measurement for the hepatic lipid content (HLC) of the subject's liver which has been obtained from the subject's liver, wherein the measurement of the subject's liver for hepatic lipid content (HLC) is obtained by using one or more of MR spectroscopy, Dixon in and out of phase imaging, or dual-echo techniques,
   a presence or absence of liver disease in the subject.

8. The system of claim 7, wherein the measured value of the subject's liver for extracellular fluid is obtained by using T1 mapping, the measurement of the subject's liver for iron content is obtained by using T2* imaging and the measurement of the subject's liver for hepatic lipid content is obtained by using MR spectroscopy.

9. The system of claim 8, wherein the measurement of the subject's liver for hepatic lipid content is obtained by using $^1$H MR spectroscopy.

10. The system of claim 8, wherein the T1 mapping is performed using a modified Look Locker inversion (MOLLI) recovery pulse sequence or a shortened modified Look Locker inversion recovery (Sh-MOLLI) sequence.

11. The system of claim 7, wherein the measurement of the subject's liver for iron content is obtained by using one or more of one or more of T2 mapping, T2* mapping, measuring one or more blood biomarkers, or MR spectroscopy.

12. The system of claim 7, wherein the liver disease consists of one or more of non-alcoholic fatty liver disease (NAFLD), non-alcoholic steatohepatitis (NASH), high hepatic lipid content, hepatic fibrosis, autoimmune hepatitis, primary biliary cirrhosis, primary sclerosing cholangitis, viral hepatitis, chronic hepatitis, drug-induced hepatitis, haemochromatosis, thalassaemia, alcoholic hepatitis, alcoholic liver cirrhosis, portal hypertension, vascular liver disease, idiopathic hepatic fibrosis, sarcoidosis, hepatic cysts, or hemangiomas.

* * * * *